United States Patent [19]

Ito

[11] Patent Number: 6,110,947
[45] Date of Patent: Aug. 29, 2000

[54] PYRROLIDINYL HYDROXAMIC ACID COMPOUNDS AND THEIR PRODUCTION PROCESS

[75] Inventor: Fumitaka Ito, Taketoyo-Cho, Japan

[73] Assignee: Pfizer Inc., New York, N.Y.

[21] Appl. No.: 09/302,097

[22] Filed: Apr. 29, 1999

Related U.S. Application Data

[62] Division of application No. 08/913,823, filed as application No. PCT/JP96/00820, Mar. 28, 1996, Pat. No. 5,952,369.

Foreign Application Priority Data

Mar. 31, 1995 [JP] Japan .......................... PCTJP9500631

[51] Int. Cl.$^7$ ................. A61K 31/4439; A61K 31/4025; C07D 401/12; C07D 409/12; C07D 407/12

[52] U.S. Cl. ...................... 514/340; 514/422; 546/276.4; 546/278.4; 548/525

[58] Field of Search .............................. 546/276.4, 278.4; 548/525; 514/340, 422

*Primary Examiner*—Patricia L. Morris
*Attorney, Agent, or Firm*—Peter C. Richardson; Paul H. Ginsburg; Jolene W. Appleman

[57] ABSTRACT

A compound of the formula:

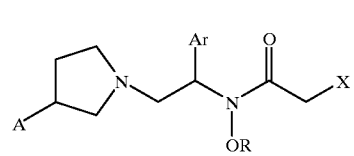

(I)

and it pharmaceutically acceptable salt, wherein

A is hydrogen, hydroxy or OY, where Y is a hydroxy protecting group;

Ar is phenyl optionally substituted with one or more substituents selected from halo, hydroxy, $C_1$–$C_4$ alkyl, $C_1$–$C_4$ alkoxy, $CF_3$, $C_1$–$C_4$ alkyloxy, and carboxy-$C_1$–$C_4$ alkyloxy;

X is phenyl, naphthyl, biphenyl, indanyl, benzofuranyl, benzothiopheny, 1-tetralone-6-yl, $C_1$–$C_4$ alkylenedioxy, pyridyl, furyl and thienyl, these groups optionally being substituted with up to three substituents selected from halo, $C_1$–$C_4$ alkyl, $C_1$–$C_4$ alkoxy, hydroxy, $NO_2$, $CF_3$ and $SO_2CH_3$; and R is hydrogen, $C_1$–$C_4$ alkyl or a hydroxy protecting group.

These compounds and pharmaceutical compositions containing them are useful as analgesic, antiinflammatory, diuretic, anesthetic or neuroprotective agents, or an agent for stroke or treatment of functional bowel diseases such as abdominal pain, for the treatment of a mammalian subject, especially a human subject. Further, the present invention provides processes for producing the hydroxamic compounds of formula (I) and their intermediate compounds of formula (II).

6 Claims, No Drawings

PYRROLIDINYL HYDROXAMIC ACID COMPOUNDS AND THEIR PRODUCTION PROCESS

CROSS REFERENCE TO RELATED APPLICATIONS

This application is a divisional of U.S. application Ser. No. 08/913,823 filed on Sep. 26, 1997, now U.S. Pat. No. 5,952,369, which is the national stage of International Application No. PCT/JP96/00820 having an international filing date of Mar. 28, 1996, designating inter alia the United States claiming priority from PCT/JP95/00631 filed on Mar. 31, 1995.

TECHNICAL FIELD

This invention relates to novel hydroxamic acid derivatives and their pharmaceutically acceptable salts, and to pharmaceutical compositions containing them. These compounds are compositions are useful as analgesic, antiinflammatory, diuretic, anesthetic or neuroprotective agents, or an agent for treatment of stroke or functional bowel disease such as abdominal pain, for the treatment of a mammalian subject, especially a human subject.

BACKGROUND ART

Opioid analgesics such as morphine are therapeutically useful, but their usage is strictly limited because of their side effects such as drug dependency. Thus, analgesics with high usefulness and reduced tendency to cause drug dependency are desired. Considerable pharmacological and biochemical studies have been carried out to discover the opioid peptides and opioid receptors, and the discovery of the subtype of opioid receptor such as $\mu$, $\delta$, $\kappa$ at a peripheral nerve in a variety of species, including human, has made a beginning towards creating new analgesics. As it is thought that opioid analgesics such as morphine act as a $\mu$-receptor agonist, separating the action based on a $\kappa$-receptor agonist from the action based on $\mu$-receptor agonist has been investigated. Recently $\kappa$-selective agonists have been reported from the above viewpoint for example, EMD-60400: A. Barber et al., Naunyn-Schmled. Arch. Pharmacol., 345 (Suppl.): Abst 456. Some of them actually have been studied in clinical trials (Med. Res. Rev., 12, 525 (1992)).

However, even when a selective $\kappa$-receptor agonist is employed, use of high doses can give rise to side effects such as sedation. Therefore, it would be desired to provide compounds having better agonist activity toward opioid $\kappa$-receptor, and in particular compounds having only low sedative activity.

BRIEF DISCLOSURE OF THE INVENTION

The present invention provides a compound of the following formula:

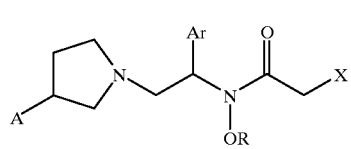

(I)

and the salts thereof, wherein

A is hydrogen, hydroxy or OY, wherein Y is a hydroxy protecting group;

Ar is phenyl optionally substituted with one or more (preferably up to three) substituents selected from halo, hydroxy, $C_1$–$C_4$ alkyl, $C_1$–$C_4$ alkoxy, $CF_3$, $C_1$–$C_4$ alkoxy-$C_1$–$C_4$ alkyloxy, and carboxy-$C_1$–$C_4$ alkyloxy;

X is phenyl, naphthyl, biphenyl, indanyl, benzofuranyl, benzothiophenyl, 1-tetralone-6-yl, $C_1$–$C_4$ alkylenedioxy, pyridyl, furyl and thienyl, these groups optionally being substituted with up to three substituents selected from halo, $C_1$–$C_4$ alkyl, $C_1$–$C_4$ alkoxy, hydroxy, $NO_2$, $CF_3$ and $SO_2CH_3$; and R is hydrogen, $C_1$–$C_4$ alkyl or a hydroxy protecting group.

The hydroxamic acid derivatives of the present invention of formula (I), wherein A is hydrogen or hydroxy and R is hydrogen or $C_1$–$C_4$ alkyl, exhibit significant agonist activity toward opioid $\kappa$-receptor. Therefore these $\kappa$ agonists are particularly useful as an analgesic agent in mammals, especially humans. They are also useful as antiinflammatory, diuretic, anesthetic or neuroprotective agents, or an agent for treatment of stroke or functional bowel diseases such as abdominal pain, for the treatment of a mammalian subject, especially a human subject.

Accordingly, the present invention also provides a pharmaceutical composition useful as an analgesic, antiinflammatory, diuretic, anesthetic or neuroprotective agent, or an agent for treatment of stroke or functional bowel diseases such as abdominal pain, for the treatment of a mammalian subject, especially a human subject, which comprises a therapeutically effective amount of a hydroxamic acid of formula (I), wherein A is hydrogen or hydroxy and R is hydrogen or $C_1$–$C_4$ alkyl, or its pharmaceutically acceptable salt together with a pharmaceutically acceptable carrier.

The compounds of formula (I), wherein either or both of OY and OR represent a protected hydroxy group, are useful as chemical intermediates to the $\kappa$ agonist of formula (I). Typical hydroxy protecting groups are benzyl, triphenylmethyl, tetrahydropyranyl, methoxymethyl and $R^1R^2R^3Si$, wherein $R^1$, $R^2$ and $R^3$ are each $C_1$–$C_6$ alkyl or phenyl.

A preferred group of $\kappa$ agonists compounds of the present invention consists of the compounds of formula (I), wherein A is hydrogen or hydroxy, Ar is phenyl, X is phenyl substituted with up to three substituents selected from chloro, methyl and $CF_3$, more preferably 3,4-dichlorophenyl, and R is hydrogen. The preferred configuration of the carbon atom to which the group Ar is attached to (S).

Preferred individual compounds of the invention are:
2-(3,4-Dichlorophenyl)-N-hydroxy-N-[1-(S)-phenyl-2-(1-pyrrolidinyl)ethyl]acetamide;
N-Hydroxy-N-[1-(S)-phenyl-2-(1-pyrrolidinyl)ethyl]-2-(2,3,6-trichlorophenyl)acetamide;
N-Hydroxy-N-[1-(S)-phenyl-2-(1-pyrrolidinyl)ethyl]-2-(4-trifluoromethylphenyl)acetamide;
N-Hydroxy-N-[1-(S)-phenyl-2-(1-pyrrolidinyl)ethyl]-2-(2,4,6-trimethylphenyl)acetamide;
2-(3,4-Dichlorophenyl)-N-hydroxy-N-[2-(3-(S)-hydroxypyrrolidin-1-yl)-1-(S)-phenylethyl]acetamide;
2-(4-Bromophenyl)-N-hydroxy-N-[2-(3-(S)-hydroxypyrrolidin-1-yl)-1-(S)-phenylethyl]acetamide;
N-Hydroxy-N-[2-(3-(S)-hydroxypyrrolidin-1-yl)-1-(S)-phenylethyl]-2-(4trifluoromethylphenyl)acetamide;
2-(4-Chlorophenyl)N-hydroxy-N-[2-(3-(S)-hydroxypyrrolidin-1yl)-1-(S)-phenylethyl]acetamide;
2-(2,3-Dichlorophenyl)-N-hydroxy-N-[2-(3-(S)-hydroxypyrrolidin-1yl)-1-(S)-phenylethyl]acetamide;

2-(2,4-Dichlorophenyl)-N-hydroxy-N-[2-(3-(S)-hydroxypyrrolidin-1yl)-1-(S)-phenylethyl]acetamide;

2-(2,5-Dichlorophenyl)-N-hydroxy-N-[2-(3-(S)-hydroxypyrrolidin-1yl)-1 -(S)-phenylethyl]acetamide;

2-(2,6-Dichlorophenyl)-N-hydroxy-N-[2-(3-(S)-hydroxypyrrolidin-1yl)-1-(S)-phenylethyl]acetamide;

N-Hydroxy-N-[2-(3-(S)-hydroxypyrrolidin-1yl)-1-(S)-phenylethyl]-2-(2,3,6-trichlorophenyl)acetamide;

2-(3,4-Dichlorophenyl)-N-[2-(3-(S)-hydroxypyrrolidin-1yl)-1-(S)-phenylethyl]acetamide; and 2-(3,4-Dichlorophenyl)-N-hydroxy-N-[2-(3-(S)-hydroxypyrrolidin-1yl)-1-(S)-phenylethyl]acetamide.

Further, the present invention provides a compound of the formula:

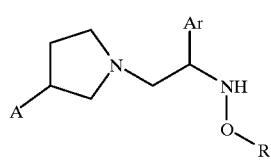

(II)

and the salts thereof, wherein

A is hydrogen, hydroxy or OY, wherein Y is hydroxy protecting group;

Ar is phenyl optionally substituted with one or more substituents selected from halo, hydroxy, $C_1$–$C_4$ alkyl, $C_1$–$C_4$ alkoxy, $CF_3$, $C_1$–$C_4$ alkoxy-$C_1$–$C_4$ alkyloxy, and carboxy-$C_1$–$C_4$ alkyloxy;

R is hydrogen, $C_1$–$C_4$ alkyl or a hydroxy protecting group.

These compounds of formula (II) can be used as intermediates to prepare the compounds of formula (I).

Further, the present invention provides processes for producing the hydroxamic compounds of formula (I) and their intermediate compounds of formula (II).

DETAILED DISCLOSURE OF THE INVENTION

The κ agonists of formula (I) of this invention can be prepared by a numbers of methods. For example, they can be readily prepared according to the procedure shown in Scheme (I).

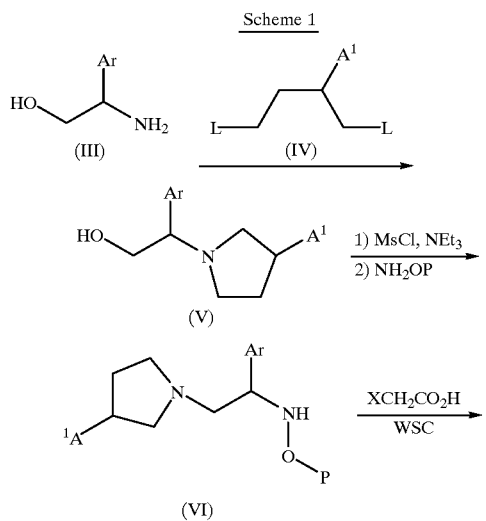

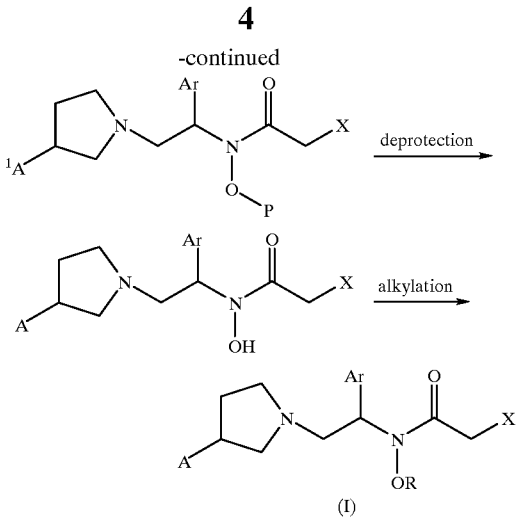

L: leaving group
P: protecting group
$A^1$: H or protected hydroxy.

Thus, the κ agonists compounds of formula (I), wherein A is hydrogen or hydroxy and R is hydrogen, can be prepared by reaction of a compound of the formula (VI) with a carboxylic acid of the formula $XCH_2COOH$, followed by removal of the protecting group P, and the protecting group in $A^1$ if necessary. This is a conventional acylation reaction, which can be carried out using standard methods, well-known to those skilled in the art. However, a convenient way of acylating a compound of formula (VI) with an acid of the formula $XCH_2COOH$ comprises coupling the two compounds in the presence of a carbodiimide compound. As especially convenient carbodiimide compound is 1-ethyl-3-(3-dimethylaminopropyl)carbodiimide hydrochloride, which is sometimes referred to as water-soluble carbodiimide, or WSC. This reaction is carried out by contacting substantially equivalent amounts of the acid and amine with a small excess of the carbodiimide in an appropriate solvent at a temperature in the range from –30 to 100° C., usually from 0 to 30° C. Appropriate solvents are inactive aromatic hydrocarbons, ethers, halogenated hydrocarbons, especially dichloromethane. The reaction takes about 30 minutes to 24 hours, usually 30 minutes to 3 hours at room temperature. The product can be isolated and purified by standard techniques.

The protecting group P, and any protecting group in $A^1$, is removed by the appropriate method for the particular protecting group chosen. Thus, a typical protecting group is benzyl. This can be removed by catalytic hydrogenation. Appropriate catalysts for hydrogenation are Pd/C, Pearlman's catalyst, Pd black, or $Pd/BaSO_4$, especially 10% Pd/C.

A further convenient protecting group for P and $A^1$ is the tetrahydropyranyl group (THP). This can be removed by acid-catalyzed hydrolysis. Appropriate acid catalysts are organic acid, inorganic acid, or Lewis acid such as AcOH, p-TsOH, HCl, $Me_2AlCl$ etc., especially HCl.

The κ agonist compounds of formula (I), wherein R is a $C_1$–$C_4$ alkyl group, can be prepared by alkylation of the corresponding compounds of formula (I), wherein R is hydroxy. This alkylation can be carried out by standard methods. A particularly convenient method involves base catalyzed alkylation using alkyl halide in the presence of phase transfer catalyst such as tetra-n-buthylammonium hydrogen sulfate. The intermediate hydroxylamine of the formula (VI) can be prepared from the alcohol (V), by treatment with methanesulfonyl chloride in the presence of a base such as triethylamine followed by addition of a protected hydroxylamine (NH$_2$OP).

The alcohol (V) is obtained from the appropriate ethanolamine compound (III) and the appropriate ethane compound of the formula (IV).

The compounds of formula (III) and (IV) are either known compounds, which can be made by the known methods, or they are analogs of known compounds, which can be prepared by methods analogous to the known methods.

The intermediate compounds of formula (II) wherein Ar is substituted phenyl can be prepared according to the procedures shown in the following Scheme 2.

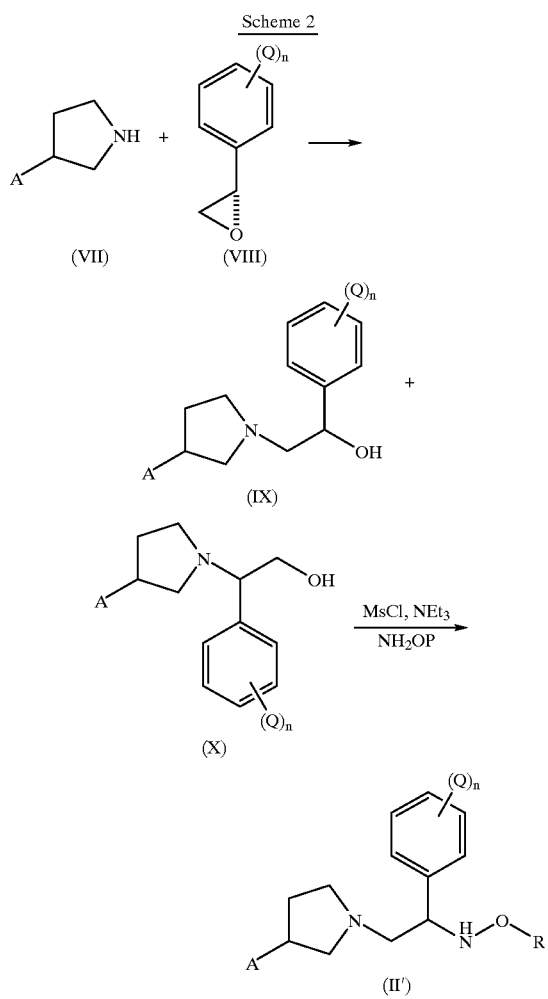

(Q is for example, halo, C$_1$–C$_4$ alkyl, C$_1$–C$_4$ alkoxy,
C$_1$–C$_4$ alkoxy-C$_1$–C$_4$ alkyloxy or CF$_3$, n=1–5, preferably 1–3)

In the above Scheme 2, a compound (VII) can be reacted with a substituted-styrene oxide (VIII) to form a mixture of a compounds (IX) and (X). This reaction may be carried out in the absence or presence of a reaction inert solvent (e.g., methanol (MeOH), ethanol (EtOH), isopropylalcohol, tetrahydrofuran (THF), dioxane, dimethylformamide (DMF), dimethylsulfoxide (DMSO), methylene chloride (CH$_2$Cl$_2$), water, benzene, toluene, n-hexane, cyclohexane) at a temperature from −78° C. to reflux temperature of the solvent, preferably from 0° C. to 25° C. for 5 minutes to 48 hours preferably from 0.5 to 12 hours. A compound (II') can be prepared from the mixture of a component (IX) and a compound (X) under the same conditions as already described in Scheme 1.

According the above procedure, R, S configuration of compounds (IX) and (X) can be selectively determined. In addition, in the above procedures, 1-substitutedphenyl-1,2-ethanediol 2-tosylate can be used instead of the substituted-styrene oxide (VIII).

The components of formula (I) of this invention are basic, and therefore they will form acid-addition salts. All such salts are within the scope of this invention. However, it is necessary to use an acid addition salts which is pharmaceutically-acceptable for administration to a mammal. The acid-addition salts can be prepared by standard methods, e.g., by contacting the basic and acidic compounds in substantially equivalent proportions in water or an organic solvent such as methanol or ethanol, or a mixture thereof. The salts can be isolated by evaporation of the solvent. Typical salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, p-toluenesulfonate, oxalate and pamoate (1,1'-methylene-bis-(2-hydroxy-3-naphtoate)) salts.

The compounds of formula (I) of this invention, wherein R is hydrogen, are acidic, and they will form base salts. All such salts are within the scope of this invention. However, it is necessary to use a base salt which is pharmaceutically-acceptable for administration to a mammale. The base salts can be prepared by standard methods, e.g., by contacting the acidic and basic compounds in substantially equivalent proportions in water or an organic solvent such as methanol or ethanol, or a mixture thereof. The salts can be isolated by evaporation of the solvent. Typical base salts which can be formed are the sodium, potassium, calcium and magnesium salts, and also salts with ammonia and amines, such as ethylamine, diethylamine, triethylamine, cyclohexylamine, piperidine and morpholine salts.

Also included within the scope of this invention are bioprecursors (also called pro-drugs) or the κ agonist compounds of the formula (I). A bioprecursor of a kappa agonist of formula (I) is a chemical derivative thereof which is readily converted back into the parent compound of formula (I) in biological systems. In particular, a bioprecursor of a κ agonist of formula (I) is converted back to the parent compound of formula (I) after the bioprecursor has been administered to, and absorbed by, a mammalian subject, e.g., a human subject. For example, it is possible to make a bioprecursor of a κ agonist of the invention of formula (I) in which one or both of A and OR is hydroxy groups by making an ester of the hydroxy group. When only one of A and OR is a hydroxy group, only mono-esters are possible. When both A and OR are hydroxy, mono- and di-esters (which can be the same or different) can be made. Typical esters are simple alkanoate esters, such as acetate, propionate, butyrate, etc. In addition, when A or OR is a hydroxy group, bioprecursors can be made by converting the hydroxy group to an acyloxymethyl derivative (e.g., a pivaloyloxymethyl derivative) by reaction with an acyloxymethyl halide (e.g., pivaloyloxymethyl chloride).

The κ agonists compounds of the present invention of formula (I) exhibit significant agonist activity toward opioid κ-receptor and are thus useful as analgesic, antiinflammatory, diuretic, anesthetic and neuroprotective agents, or an agent for treatment of stroke or functional bowel diseases such as abdominal pain, for the treatment of a mammalian subject, especially a human subject, for the treatment of mammals, especially humans in need of such agents.

The activity of the κ-agonists compounds of formula (I) of the present invention, is demonstrated by the opioid receptor binding activity. Such activity may be determined in homogenates from guinea pig whole brain, as described by Regina, A. et al. in J. Receptor Res. 12: 171–180, 1992. In summary, tissue homogenate is incubated at 25° C. for 30 min in the presence of labelled ligand and test compounds. The μ-sites are labelled by 1 nM of (3H)-[D-Ala2, MePhe4, Gly-ol5]enkephalin (DAMGO), the δ-sites by 1 nM of (3H)-[D-Pen2,5]enkephalin (DPDPE) and the κ-sites by 0.5 nM (3H)-CI-977. The non specific binding is measured by use of 1 mM CI-977 (κ), 1 mM (DAMGO) (μ), 1 mM (DPDPE) (δ). Data are expressed as the $IC_{50}$ values obtained by a non-linear fitting program using the Cheng and Prusoff equation. Some compounds prepared in the Examples showed a low $IC_{50}$ value in the range of 0.01 to 100 nM.

The activity of the κ agonists compounds can also be demonstrated by the Formalin Test as described by Wheeler-Aceto, H. et al. in Psychopharmacology 104: 35–44, 1991. In this testing, male SD rats (80–100 g) are injected s.c. with a test compound dissolved in 0.1% methyl cellulose saline or vehicle. After 30 min., 50 ml of a 2% formalin are injected into a hind paw. The number of licking the injected paw per observation period is measured 15–30 min. after the injection of formalin and expressed as % inhibition compared to the respective vehicle group.

The activity of the κ agonists can also be demonstrated by the Rotarod Test as described by Hayes, A. G. et al. in Br. J. Pharmacol. 79: 731–736, 1983. In this testing, a group of 6–10 male SD rats (100–120 g) are selected for their ability to balance on a rotating rod (diameter 9 cm, rate of rotation 5 r.p.m.). The selected rats are then injected s.c. with a test compound dissolved in 0.1% methyl cellulose saline. The animals are tested again 30 min. after treatment; a rat falling off the bar more than twice within 150 seconds is considered to be showing motor impairment and the animal's performance (i.e., time on the rotarod) are recorded. The $ED_{50}$ value, defined as the dose of the drug which halves the performance time is observed in the control group.

The κ agonists compounds of formula (I) of this invention can be administered via either the oral, parenteral or topical routes to mammals. In general, these compounds are most desirably administered to humans in doses ranging from 0.01 mg to 50 mg per day, although variations will necessarily occur depending upon the weight and condition of the subject being treated, the disease state being treated and the particular route of administration chosen. However, a dosage level that is in the range of from 0.01 mg to 1 mg per kg of body weight per day, single or divided dosage is most desirably employed in humans for the treatment of pain in a postoperative patient.

The compounds of the present invention may be administrated alone or in combination with pharmaceutically acceptable carriers or diluents by either of the above route previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES AND PREPARATIONS

The present invention is illustrated by the following examples and preparations. However, it should be understood that the invention is not limited to the specific details of these examples and preparations. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Preparation 1

(S)-N-Benzyloxy-1-phenyl-2-pyrrolidinoethylamine

To a stirred solution of (R)-2-phenyl-2-pyrrolidinoethanol (E. Brown et al, Tetrahedron: Asymmetry, 1991, 2, 339, 4.78 g, 25 mmol) and triethylamine (3.95 ml, 28 mmol) in $CH_2Cl_2$ (50 ml) was added methanesulfonyl chloride (2 ml, 26 mmol) dropwise at 0° C. (ice bath). After 3 h stirring at 0° C. to room temperature (rt), the reaction mixture was washed with saturated NaHCO$_3$ aqueous solution, dried (Na$_2$SO$_4$), and concentrated to give 5.88 g of yellow solid and brown viscous oil mixture. To this mixture was added O-benzylhydroxylamine (this was prepared from O-benzylhydroxylamine hydrochloride 5.99 g (37.5 mmol) by basification) and ethanol 6 ml) and the mixture was stirred at 80° C. for 1 h. The solvent was evaporated to give 9.47 g of white solid which was collected by filtration and washed with ethanol/ether to afford 6.96 g (83.7%) of hydrochloride salt of desired product as white crystalline, mp 161–162° C.

$^1$H NMR (270 MHz, CDCl$_3$) d 7.44–7.25 (10 H, m), 6.40 (1H, br.s), 4.68 (1H, d, J=11.7 Hz), 4.68–4.62 (1H, m), 4.63 (1H, d, J=11.7 Hz), 3.90–3.70 (1H, m), 3.60 (1H, dd, J=7.7, 13.2 Hz), 3.55–3.40 (1H, m), 3.05 (1H, dd, J=5.5, 13.2 Hz), 2.80–2.65 (1H, m), 2.65–2.45 (1H, m), 2.25–2.05 (2H, m), 2.05–1.80 (3H, m). Anal. Calcd for C$_{19}$H$_{24}$N$_2$O.HCl: C, 68.56; H, 7.57; N, 8.42; Cl, 10.65.

Found: C, 68.36; H, 7.70; N, 8.39; Cl, 11.13.

This hydrochloride salt (80 mg) was basified with ammonium hydroxide solution, extracted with CH$_2$Cl$_2$, dried (Na$_2$SO$_4$), and concentrated to give 67 mg of free amine derivative as a colorless oil.

$^1$H NMR (270 MHz, CDCl$_3$) δ7.46–7.12 (10H, m), 6.53 (1H, br.s), 4.53 (1H, d, J=11.0 Hz), 4.45 (1H, d, J=11.4 Hz), 4.20 (1H, dd, J=3.7, 11.4 Hz), 2.90 (1H, dd, J=11.4, 12.5 Hz), 2.70–2.60 (2H, m), 2.50–2.35 (2H, m), 2.28 (1H, dd, J=4.0, 12.5 Hz), 1.80–1.70 (4H, m).

IR(neat): 3250 cm$^{-1}$.

[α]$_D$=+44.6 (c=0.67, MeOH).

EXAMPLE 1

N-Benzyloxy-2-(3,4-dichlorophenyl)-N-[1-(S)-phenyl-2-(1pyrrolidinyl)ethyl]acetamide To a stirred solution of (S)-1-(2-O-benzylhydroxylamino-2-phenyl-ethyl)pyrrolidine hydrochloride (2.88 g, 8.65 mmol) and 3,4-dichlorophenylacetic acid (2.05 g, 10 mmol) in CH$_2$Cl$_2$ (30 ml) was added 1-ethyl-3-(3-dimethylaminopropyl)carbodiimide hydrochloride (2.30 g, 12 mmol) at room temperature. After 1 hr stirring, the reaction mixture was washed with water and saturated NaHCO$_3$ aqueous solution, dried (Na$_2$SO$_4$), and concentrated to give 4.44 g of pale brown viscous oil. To this oil was added methanol (2 ml) and stood for 1 hr. The white crystalline appeared was collected by filtration to give 1.60 g of white powder. The filtrate was concentrated to afford 2.84 g of oil and solid mixture, which was purified by column chromatography (silica gel; 100 g, CH$_2$Cl$_2$/MeOH; 40/1) to give 0.82 g of clear yellow viscous oil, which was crystallized by addition of methanol (0.2 ml).

Total yield was 2.42 g (57.9%). mp 88.5–90° C.

$^1$H NMR (270 MHz, CDCl$_3$) δ7.46–7.21 (12H, m), 6.98 (1H, dd, J=2.2, 8.4 Hz), 5.80–5.65 (1H, m), 4.73 (1H, d, J=10.3 Hz), 4.43 (1H, d, J=10.6 Hz), 3.77 (1H, d, J=15.8 Hz), 3.61–3.51 (2H, m, including 1H, d, J=15.4 Hz at 3.54 ppm), 2.75–2.60 (3H, m), 2.55–2.40 (2H, m), 1.80–1.50 (4H, m). IR(Nujol): 1670 cm$^{-1}$.

EXAMPLE 2

2-(3,4-Dichlorophenyl)-N-hydroxy-N-[1-(S)-phenyl-2-(1-pyrrolidinyl)ethyl]acetamide A suspension mixture of N-benzyloxy-2-(3,4-dichlorophenyl)-N-[1-(S)-phenyl-2-(1-pyrrolidinyl)ethyl] acetamide (1.60 g, 3.3 mmol), 10% palladium on carbon (0.16 g), and HCl gas saturated methanol (20 ml) in methanol (20 ml) was stirred under hydrogen atmosphere at room temperature for 13 h. After removal of the catalyst by Celite filtration, the filtrate was concentrated to give 1.63 g of violet colored viscous oil, which was basified with NH$_4$OH and extracted with CH$_2$Cl$_2$ (20 ml×3). The extract combined was dried (Na$_2$SO$_4$) and concentrated to afford a brown colored crystalline, which was collected by filtration and washed with ether/hexane to give 1.04 g (80%) of pale yellow powder, mp 118–120° C.

$^1$H NMR (270 MHz, CDCl$_3$) δ7.44 (1H, d, J=1.8 Hz), 7.37–7.24 (6H, m, including 1H, d, J=8.4 Hz at 7.36 ppm), 7.17 (1H, dd, J=1.8, 8.4 Hz), 5.56 (1H, dd, J=5.9, 10.3 Hz), 3.90 (1H, d, J=14.3 Hz), 3.70 (1H, d, J=13.9 Hz), 3.31 (1H, dd, J=10.6, 12.5 Hz), 2.73 (1H, dd, J=5.9, 12.5 Hz), 2.60–2.45 (4H, m), 1.80–1.55 (4H, m).

IR(CH$_2$Cl$_2$): 3450, 1650 cm$^{-1}$.

MS m/z: 394 (M$^+$+2, 0.48), 392(M$^+$, 1.1), 211(4.8), 173(3.1), 149(12.9), 132(12.8), 99(28.8), 84(100).

925 mg of this crystalline was dissolved in CH$_2$Cl$_2$ (10 ml). To this solution was added HCl gas saturated ether (10 ml) at room temperature. The mixture solution was concentrated to give a white crystalline, which was collected by filtration and washed with ether to afford 971 mg of HCl salt as white powder.

mp 161–162° C.

[α]$_D$=+119.8(c=0.884, MeOH).

Anal. Calcd for C$_{20}$H$_{22}$Cl$_2$N$_2$O$_2$.HCl.0.5H$_2$O: C, 54.75; 5.51; N, 6.38

Found: C, 54.96; H, 5.49; N, 6.44.

EXAMPLE 3

2-(3,4-Dichlorophenyl)-N-methoxy-N-[1-(S)-phenyl-2-(1-pyrrolidinyl)ethyl]acetamide A mixture of 2-(3,4-Dichlorophenyl)-N-hydroxy-N-[1-(S)-phenyl-2-(1-pyrrolidinyl)ethyl]acetamide (598 mg, 1.5 mmol), tetrabutylammonium hydrogen sulfate (10 mg), NaOH 50% aqueous solution (1 ml), and iodomethane (0.12 ml, 2 mmol) in toluene (4 ml) was stirred at room temperature for 3 h. The mixture was extracted with ethyl acetate (20 ml×2). The extract combined was washed with brine, dried (Na$_2$SO$_4$) and concentrated to afford 1.06 g of brown viscous oil, which was purified by column chromatography (silica gel 60 g, CH$_2$Cl$_2$/MeOH: 20/1) to give 304 mg (49.8%) of yellow viscous oil.

$^1$H NMR (270 MHz, CDCl$_3$) δ7.41–7.26 (7H, m), 7.09 (1H, dd, J=1.8, 8.1 Hz), 5.70–5.60 (1H, m), 3.83 (1H, d, J=15.4 Hz), 3.65 (1H, d, J=15.4 Hz), 3.50 (3H, s), 3.50 (1H, dd, J=9.9, 12.5 Hz), 2.75–2.57 (3H, m, including 1H, dd, J=4.8, 12.5 Hz at 2.60 ppm), 2.55–2.40 (2H, m), 1.70 (4H, m).

IR(neat): 1670 cm$^{-1}$.

304 mg of this crystalline was dissolved in MeOH (5 ml). To this solution was added HCl gas saturated ether (5 ml) at room temperature. The mixture solution was concentrated to give a white crystalline, which was collected by filtration and washed with ether to afford 277 mg of HCl salt as white powder.

mp 165–166° C. Anal. Calcd for C$_{21}$H$_{24}$Cl$_2$N$_2$O$_2$.HCl.0.5H$_2$O: C, 55.70; 5.79; N, 6.19

Found: C, 55.53; H, 5.80; N, 6.19.

EXAMPLE 4

N-Hydroxy-N-[1-(S)-phenyl-2-(1-pyrrolidinyl) ethyl]-2-(2,3,6-trichlorophenyl)acetamide This was prepared from (S)-1-(2-O-benzylhydroxylamino-2-phenylethyl)pyrrolidine in 68% yield according to a procedure similar to that described in Examples 2 and 3.

mp 217–218.5° C. (HCl salt)

$^1$H NMR (270 MHz, free amine, CDCl$_3$) δ7.44–7.20 (8H, m), 5.61 (1H, dd, J=5.9, 10.6 Hz), 4.36 (1H, d, J=16.9 Hz), 4.26 (1H, d, J=17.2 Hz), 3.40 (1H, dd, J=10.6, 12.5 Hz), 2.80 (1H, dd, J=5.9, 12.5 Hz), 2.76–2.55 (4H, m), 1.90–1.70 (4H, m).

IR(neat, free amine): 1650 cm$^{-1}$.

Anal. Calcd for C$_{20}$H$_{21}$Cl$_3$N$_2$O$_2$.HCl.0.5H$_2$O: C, 50.76; 4.90; N, 5.92

Found: C, 50.58; H, 4.65; N, 5.83.

EXAMPLE 5

N-Hydroxy-N-[1-(S)-phenyl-2-(1-pyrrolidinyl) ethyl]-2-(4-trifluoromethylphenyl)acetamide This was prepared from (S)-1-(2-O-benzylhydroxylamino-2-phenylethyl)pyrrolidine in 66.6% yield according to a procedure similar to that described in Examples 2 and 3.

mp 172.8–177° C. (HCl salt)

$^1$H NMR (270 MHz, free amine, CDCl$_3$) δ7.55 (2H, d, J=8.4 Hz), 7.45 (2H, d, J=8.1 Hz), 7.40–7.20 (6H, m), 5.57 (1H, dd, J=5.9, 10.3 Hz), 4.00 (1H, d, J=13.9 Hz), 3.81 (1H, d, J=13.9 Hz), 3.30 (1H, dd, J=10.6, 12.5 Hz), 2.71 (1H, dd, J=5.9, 12.5 Hz), 2.60–2.40 (4H, m), 1.80–1.50 (4H, m).

IR(neat, free amine): 3150, 1650 cm$^{-1}$.

Anal. Calcd for C$_{21}$H$_{23}$F$_3$N$_2$O$_2$.H$_2$O: C, 56.44; 5.86; N, 6.27

Found: C, 56.16; H, 5.77; N, 6.76.

EXAMPLE 6

N-Hydroxy-2-(1-naphthyl)-N-[1-(S)-Phenyl-2-(1pyrrolidinyl)ethyl]acetamide

This was prepared from (S)-1-(2-O-benzylthydroxylamino-2-phenylethyl)pyrrolidine in 65.1% yield according to a procedure similar to that described in Examples 2 and 3.

mp 81.0–83.5° C. (HCl salt)

$^1$H NMR (270 MHz, free amine, CDCl$_3$) δ7.55–7.20 (13H, m), 5.59 (1H, dd, J=5.9, 10.3 Hz), 4.43 (1H, d, J=14.7 Hz), 4.10 (1H, d, J=15.0 Hz), 3.31 (1H, dd, J=11.0, 12.1 Hz), 2.65 (1H, dd, J=5.9, 12.5 Hz), 2.55–2.35 (4H, m), 1.60–1.35 (4H, m).

IR (neat, free amine): 3150, 1650 cm$^{-1}$.

Anal. Calcd for C$_{24}$H$_{26}$N$_2$O$_2$.HCl.1.2H$_2$O: C, 66.64; 6.85; N, 6.48

Found: C, 66.93; H, 6.50; N, 6.02.

EXAMPLE 7

N-Hydroxy-N-[1-(S)-phenyl-2-(1-pyrrolidinyl) ethyl]-2-(2,4,6-trimethylphenyl)acetamide This was prepared from (S)-1-(2-O-benzylhydroxylamino-2-phenylethyl)pyrrolidine in 58.9% yield according to a procedure similar to that described in Examples 2 and 3.

mp 186–187.2° C. (HCl salt).

$^1$H NMR (270 MHz, free amine, CDCl$_3$) δ7.42–7.24 (6H, m), 6.82 (2H, s), 5.70–5.55 (1H, m), 3.86 (2H, br.s), 3.38 (1H, dd, J=10.6, 12.1 Hz), 2.74 (1H, dd, J=5.9, 12.5 Hz), 2.70–2.55 (4H, m), 2.22 (9H, s), 1.85–1.75 (4H, m).

IR(neat, free amine): 3220, 1640 cm$^{-1}$.

Anal. Calcd for C$_{23}$H$_{30}$N$_2$O$_2$.HCl.1.3H$_2$O: C, 64.79; 7.94; N, 6.57

Found: C, 64.51; H, 7.48; N, 6.31.

EXAMPLE 8

N-Hydroxy-2-(4-pyridyl)-N-[1-(S)-phenyl-2-(1-pyrrolidinyl)ethyl]acetamide

This was prepared from (S)-1-(2-O-benzylhydroxylamino-2-phenylethyl)pyrrolidine in 67.9% yield according to a procedure similar to that described in Examples 2 and 3.

$^1$H NMR (270 MHz, free amine, CDCl$_3$) δ8.46 (2H, d, J=5.9 Hz), 7.40–7.18 (8H, m), 5.61 (1H, dd, J=5.5, 10.6 Hz), 3.91 (1H, d, J=14.3 Hz), 3.77 (1H, d, J=13.9 Hz), 3.33 (1H, dd, J=11.0, 12.1 Hz), 2.68 (1H, dd, J=5.5, 12.5 Hz), 2.57–2.40 (4H, m), 1.80–1.55 (4H, m).

IR(neat, free amine): 1640 cm$^{-1}$.

EXAMPLE 9

2-(Benzo[b]furan-4yl)-N-hydroxy-N-[1-(S)-phenyl-2-(1-pyrrolidinyl)ethyl]acetamide This was prepared from (S)-1-(2-O-benzylhydroxylamino-2-phenylethyl)pyrrolidine in 73.5% yield according to a procedure similar to that described in Examples 2 and 2.

$^1$H NMR (270 MHz, CDCl$_3$) δ7.59 (1H, d, J=1.8 Hz), 7.45–7.20 (9H, m), 6.98 (1H, br.s), 5.58 (1H, dd, J=5.9, 10.6 Hz), 4.24 (1H, d,, J=13.6 Hz), 3.91 (1H, d, J=13.6 Hz), 3.28 (1H, d,d, J=11.3, 11.7 Hz), 2.60 (1H, dd, J=5.9, 12.5 Hz), 2.45–2.30 (4H, m), 1.60–1.30 (4H, m).

IR(neat, free amine): 1650 cm$^{-1}$.

Preparation 2
1,4-Diiodo-2-(S)-(tetrahydropyranyloxy)butane

To a stirred solution of (S)-(−)-1,2,4-butaneutriol (10.61, 0.1 mol) in pyridine (100 ml) was added p-toluenesulfonyl choride (38.13 g, 0.2 mol) by portions at 0° C. After 2h stirring, the reaction mixture was poured into 10% HCl aqueous solution including ice and acidified to pH2. The mixture was extracted with ethyl acetate (150 ml×3). The extract combined was washed with brine, dried (Na$_2$SO$_4$), and concentrated to give 42.88 g of colorless oil. A mixture of this crude ditosylate (42.88 g, 0.1 mol) and NaI (44.97 g, 0.3 mol) in acetone (300 ml) was refluxed with stirring for 5 h. The solid precipitated was removed by filtration and the filtrate was concentrated. The residue was dissolved in ethyl acetate and washed with Na$_2$S$_2$O$_3$ aqueous solution and brine. After dry (Na$_2$SO$_4$), the solvent was evaporated and the residue was purified by column chromatography (silica gel 250 g, hexane/ethyl acetate: 10/1) to afford 24.81 g of colorless oil. A mixture of this oil (24.8 g, 76.1 mmol), 3,4-dihydro-2H-pyran (21.9 ml, 0.24 mol), and pyridinium p-toluenesulfonate (125 mg) in CH$_2$Cl$_2$ (100 ml) was stirred at room temperature for 12 h. The reaction mixture was diluted with CH$_2$Cl$_2$ (100 ml), washed with NaHCO$_3$ aqueous solution, and dried (NaSO$_4$). Evaporation of the solvent gave 33.56 g of pale yellow oil, which was purified by column chromato-graphy (silica gel 250 g, hexane/ethyl acetate: 20/1) to afford 28.75 g (70.1% for 3 steps) of colorless oil.

$^1$H NMR (270 MHz, CDCl$_3$) δ4.80–4.75 (1H, m), 4.02–3.85 (1H, m), 3.70–3.17 (6H, m), 2.27–2.01 (2H, m), 1.90–1.55 (6H, m).

Preparation 3

2-(R)-Phenyl-2-(3-(S)-tetrahydropyranyloxypyrrolidin-1-yl)ethanol

A suspension mixture of 1,4-diiido-2-(S)-(tetrahydropyranyloxyl)-butane (12.50 g, 30 mmol), R-(–)-phenylglycinol (3.43 g, 25 mmol), and $K_2CO_3$ (6.91 g, 50 mmol) in ethanol (50 ml) was refluxed with stirring for 6 h. The white solid was removed by filtration and the filtrate was concentrated. The residue was diluted with $NaHCO_3$ aqueous solution (30 ml) and extracted with $CH_2Cl_2$ (20 ml×3). After dry ($Na_2SO_4$), the solvent was evaporated to give 9.54 g of clear yellow oil, which was purified by column chromatography (silica gel 150 g, $CH_2Cl_2$/MeOH: 20/1) to afford 7.22 g (99%) of colorless viscous oil.

$^1$H NMR (270 MHz, $CDCl_3$) δ7.37–7.27 (5H, m), 4.61–4.51 (1H, m), 4.40–4.28 (1H, m), 3.91–3.75 (3H, m), 3.55–3.42 (2H, m), 2.92–2.72 (1H, m), 2.70–2.57 (2H, m), 2.55–2.25 (2H, m), 2.20–1.95 (1H, m), 1.93–1.60 (3H, m), 1.60–1.45 (4H, m).

IR(neat): 3450 $cm^{-1}$.

Preparation 4

1-(S)-Phenyl-N-tetrahydropyranyloxy-2-(3-(S)-tetrahydropyranyloxypyrrolidin-1-yl)ethylamine This was prepared from 2-(R)-phenyl-2-(3-(S)-tetrahydro-pyranyloxypyrrolidin-1-yl)ethanol and O-tetrahydropyranyl-hydroxylamine (R. N. Warrener and E. N. Cain, Angew. Chem. Int. Edit. 1966, 5, 511) in 42.5% yield as a brown oil according to a procedure similar to that described in Preparation 1.

$^1$H NMR (270 MHz, $CDCl_3$) δ7.45–7.25 (5H, m), 6.51 (1H, br.s), 4.80–4.73 (1H, m), 4.65–4.55 (1H, m), 4.45–4.33 (1H, m), 4.28–4.15 (1H, m), 4.00–3.75 (2H, m), 3.70–2.55 (9H, m), 2.30–2.05 (1H, m), 1.90–1.35 (12H, m).

EXAMPLE 10

2-(3,4-Dichlorophenyl)-N-tetrahydropyranyloxy-N-[2-(3-(S)-tetrahydropyranyloxypyrrolidin-1-yl)-1-(S)-phenylethyl]acetamide This was prepared from 1-(S)-Phenyl-N-tetrahydropyranyloxy-2-(3-(S)-tetrahydropyranyloxypyrrolidin-1-yl)ethylamine and 3,4-dichlorophenylacetic acid in 69.8% yield as a clear brown viscous oil according to a procedure similar to that described in Example 1.

$^1$H NMR (270 MHz, $CDCl_3$) δ7.43–7.15 (7.4H, m), 6.98–6.91 (0.6H, m), 5.69 (0.4H, dd, J=4.0, 11.0 Hz), 5.58 (0.6H, dd, J=11.4 Hz), 5.35–5.20 (1H, m), 4.65–4.53 (1H, m), 4.41–4.21 (1H, m), 4.15–3.80 (4H, m), 3.68–3.10 (4H, m), 3.03–2.80 (2H, m), 2.70–2.35 (3H, m), 2.20–1.10 (13H, m).

IR(neat): 1660 $cm^{-1}$.

EXAMPLE 11

2-(3,4-Dichlorophenyl)-N-hydroxy-N-[2-(3-(S)-hydroxypyrrolidin-1-yl)-1-(S)-phenylethyl]acetamide A mixture of 2-(3,4-Dichlorophenyl)-N-tetrahydropyranyloxy-N-[2-(3-(S)-tetrahydropyranyloxypyrrolidin-1-yl)-1-(S)-phenylethyl]acetamide (1.13 g, 1.96 mmol) and HCl gas saturated MeOH (4 ml) in MeOH (20 ml) was stirred at room temperature for 7 h. The solvent was evaporated. The residue was basified with saturated $NaHCO_3$ aqueous solution, extracted with $CH_2Cl_2$, and dried ($Na_2SO_4$). Evaporation of the solvent gave 0.80 g of brown viscous oil, which was crystallized by adding ether and scratching. The crystalline was collected by filtration and washed with ether to afford 377 mg (47.1%) of white powder.

mp 98.5–99.5° C.

$^1$H NMR (270 MHz, $CDCl_3$) δ7.45–7.20 (7H, m), 7.14 (1H, dd, J=1.8, 9.9 Hz), 5.62 (1H, dd, J=5.5, 11.0 Hz), 5.00–3.00 (2H, almost flat br.s), 4.35–4.25 (1H, m), 3.85 (1H, d, J=14.3 Hz), 3.73 (1H, d, J=13.9 Hz), 3.38 (1H, dd, J=11.0, 12.5 Hz), 2.95 (1H; dt, J=5.1, 8.8 Hz), 2.73 (1H, d, J=10.6 Hz), 2.65 (1H, dd, J=5.5, 12.5 Hz), 2.51 (1H, dd, J=5.5, 10.6 Hz), 2.40–2.27 (1H, m), 2.22–2.07 (1H, m), 1.65–1.50 (1H, m).

IR(Nujol): 3070, 1640 $cm^{-1}$.

MS m/z: 412($M^+$+4, 10.3), 410($M^+$+2, 85.7), 408($M^+$, 100), 304(8.6), 149(50.2), 114(22.7), 112(24.2).

$[α]_D$=+102.9(c=0.516, MeOH).

HCl salt: mp 65.5–67.0° C.

Anal. Calcd for $C_{20}H_{22}Cl_2N_2O_3 \cdot HCl \cdot 0.5H_2O$: C, 52.82, H, 5.32; N, 6.16.

Found: C, 53.09; H, 5.29; N, 6.17.

Preparation 5

(R)-(–)-2-(4-Fluorophenyl)glycinol

This was prepared from 4-fluoro-D-a-phenylglycine in 88% yield according to the procedure of D. A. Evans (Organic Synthesis, 68, 77). $^1$H NMR (270 MHz, $CDCl_3$) δ7.30 (2H, dd, J=5.5, 8.4 Hz), 7.03 (2H, t, J=8.4 Hz), 4.05 (1H, dd, J=4.4, 8.1 Hz), 3.71 (1H, dd, J=4.4, 10.6 Hz), 3.53 (1H, dd, J=8.4, 10.6 Hz), 2.19 (3H, br.s).

IR(KBr): 3350, 3280 $cm^{-1}$.

Preparation 6

2-(R)-(4-Fluorophenyl)-2-(3-(S)-tetrahydropyranyloxypyrrolidin-1-yl)ethanol

This was prepared from (R)-(–)-2-(4-fluorophenyl)glycinol in 68.8% yield according to a procedure similar to that described in Preparation 3.

$^1$H NMR (270 MHz, $CDCl_3$) δ7.31–7.26 (2H, m), 7.03 (2H, dd, J=8.4, 8.8 Hz), 4.65–4.51 (1H, m), 4.40–4.27 (1H, m), 3.90–3.75 (3H, m), 3.55–3.40 (2H, m), 2.90–2.70 (1H, m), 2.70–2.50 (2H, m), 2.50–2.35 (1H, m), 2.30–1.95 (2H, m), 1.95–1.60 (3H, m), 1.60–1.45 (4H, m).

IR(neat): 3450 $cm^{-1}$.

EXAMPLE 12

2(3,4-Dichlorophenyl)-N-[1-(S)-(4-fluorophenyl)ethyl-2-(3-(S)-hydroxypyrrolidin-1-yl]-N-hydroxyacetamide This was prepared from 2-(R)-(4-fluorophenyl)-2-(3-(S)-tetrahydropyranyloxypyrrolidin-1-yl)ethanol and 3,4-dichlorophenylacetic acid in 52.8% yield according to a procedure similar to that described in Preparation 4, Examples 10 and 11.

$^1$NMR (270 MHz, $CDCl_3$) δ7.41–7.26 (4H, m), 7.12 (1H, dd, J=1.8, 8.1 Hz), 6.99 (2H, dd, J=8.4, 8.8 Hz), 5.60 (1H, dd, J=5.1, 11.0 Hz), 4.35–4.25 (1H, m), 3.82 (1H, d, J=13.9 Hz), 3.72 (1H, d, J=14.3 Hz), 3.71 (1H, s), 3.58 (1H, s), 3.35 (1H, dd, J=11.7, 12.1 Hz), 3.00–2.90 (1H, m), 2.73 (1H, br.d, J=11.0 Hz), 2.58 (1H, dd, J=5.1, 12.5 Hz), 2.51 (1H, dd, J=5.5, 10.6 Hz), 2.37–2.10 (2H, m), 1.65–1.55 (1H, m).

IR(neat): 3200, 1640 $cm^{-1}$.

MS m/z: 426($M^+$).

HCl salt: amorphous solid.

Anal. Calcd for $C_{20}H_{21}Cl_2FN_2O_3 \cdot HCl \cdot 0.7H_2O$: C, 50.43; H, 4.95; N, 5.88.

Found: C, 50.80; H, 4.96; N, 5.45.

EXAMPLE 13

2-(4-Bromophenyl)-N-hydroxy-N-[2-(3-(S)-hydroxypyrrolidin-1-yl)-1-(S)-phenylethyl] acetamide This was prepared from 2-(R)-phenyl-2-(3-(S)-tetrahydropyranyloxypyrrolidin-1-yl)ethanol and 4-bromophenylacetic acid in 44.6% yield according to a procedure similar to that described in Preparation 4, Examples 10 and 11.

$^1$H NMR (270 MHz, CDCl$_3$) δ7.50–7.14 (9H, m), 5.61 (1H, dd, J=5.1, 11.0 Hz), 4.28–4.22 (1H, m), 3.90 (1H, d, J=13.6 Hz), 3.70 (1H, d, J=13.9 Hz), 3.33 (1H, dd, J=11.0, 12.5 Hz), 2.92–2.82 (1H, m), 2.72–2.64 (2H, m), 2.50 (1H, dd, J=5.5, 10.6 Hz), 2.38–2.28 (1H, m), 2.20 (2H, br.s), 2.16–2.01 (1H, m), 1.60–1.50 (1H, m).

IR(neat): 3200, 1630 cm$^{-1}$.

MS m/z: 418(M$^+$).

HCl salt: amorphous solid.

Anal. Calcd for $C_{20}H_{23}BrN_2O_3 \cdot HCl \cdot 0.5H_2O$: C, 51.68; H, 5.42; N, 6.01.

Found: C, 51.75; H, 5.51; N, 5.71.

EXAMPLE 14

2-(3-Bromophenyl)-N-hydroxy-N-[2-(3-(S)-hydroxypyrrolidin-1-(S)-phenylethyl]acetamide This was prepared from 2-(R)-phenyl-2-(3-(S)-tetrahydropyranyloxypyrrolidin-1 -yl)ethanol and 3-bromophenylacetic acid in 29.8% yield according to a procedure similar to that described in Preparation 4, Examples 10 and 11.

$^1$H NMR (270 MHz, CDCl$_3$) δ7.51–7.15 (9H, m), 5.62 (1H, dd, J=5.5, 11.0 Hz), 4.28–4.20 (1H, m), 3.94 (1H, d, J=13.9 Hz), 3.70 (1H, d, J=13.6 Hz), 3.35 (1H, dd, J=11.4, 12.5 Hz), 2.92–2.83 (1H, m), 2.70–2.62 (2H, m), 2.51 (1H, dd, J=5.1, 10.6 Hz), 2.42 (2H, br.s), 2.38–2.28 (1H, m), 2.18–2.03 (1H, m), 1.60–1.46 (1H, m).

IR(neat): 3200, 1630 cm$^{-1}$.

MS m/z: 418(M$^+$).

HCl salt: amorphous solid.

Anal. Calcd for $C_{20}H_{23}BrN_2O_3 \cdot HCl \cdot H_2O$: C, 50.70; H, 5.53; N, 5.91.

Found: C, 50.57; H, 5.58; N, 5.90.

EXAMPLE 15

2-(4-Fluorophenyl)-N-hydroxy-N-[2-(3-(S)-hydroxypyrrolidin-1yl)-1-(S)-phenylethyl]acetamide This was prepared from 2-(R)-phenyl-2-(3-(S)-tetrahydropyranyloxypyrrolidin-1-yl)ethanol and 4-fluorophenylacetic acid in 23.6% yield according to a procedure similar to that described in Preparation 4, Examples 10 and 11.

$^1$H NMR (270 MHz, CDCl$_3$) δ7.40–7.22 (7H, m), 7.10–6.95 (2H, m), 5.67–5.61 (1H, m), 4.34–4.22 (1H, m), 3.92 (1H, d, J=13.6 Hz), 3.73 (1H, d, J=13.9 Hz), 3.36 (1H, dd, J=10.6, 12.5 Hz), 2.96–2.86 (1H, m), 2.76–2.62 (2H, m), 2.58–2.48 (1H, m), 2.40–2.28 (1H, m), 2.24–1.70 (3H, m), 1.64–1.48 (1H, m).

IR(neat): 3400, 1630 cm$^{-1}$.

MS m/z: 358(M$^+$).

HCl salt: amorphous solid.

Anal. Calcd for $C_{20}H_{23}FN_2O_3 \cdot HCl \cdot 0.4H_2O$: C, 59.74; H, 6.22; N, 6.97.

Found: C, 59.81; H, 6.43; N, 6.88.

EXAMPLE 16

2-(3,4-Dimethoxyphenyl)-N-hydroxy-N-[2-(3-(S)-hydroxypyrrolidin-1-yl)-1-(S)-phenylethyl] acetamide This was prepared from 2-(R)-phenyl-2-(3-(S)-tetrahydropyranyloxypyrrolidin-1-yl)ethanol and 3,4-dimethoxyphenylacetic acid in 10.6% yield according to a procedure similar to that described in Preparation 1, Examples 10 and 11.

$^1$H NMR (270 MHz, CDCl$_3$) δ7.40–7.22 (5H, m), 6.95–6.78 (3H, m), 5.70–5.60 (1H, m), 4.25–4.15 (1H, m), 3.91 (1H, d, J=13.9 Hz), 3.88 (3H, s), 3.87 (3H, s), 3.68 (1H, d, J=13.9 Hz), 3.33 (1H, dd, J=11.4, 11.7 Hz), 2.90–2.78 (1H, m), 2.74–2.60 (2H, m), 2.47 (1H, dd, J=5.1, 10.6 Hz), 2.34–2.20 (1H, m), 2.14–1.98 (1H, m), 1.90 (2H, br.s), 1.50–1.36 (1H, m).

IR(neat): 3400, 1640 cm$^{-1}$.

MS m/z: 400(M$^+$).

HCl salt: amorphous solid.

Anal. Calcd for $C_{22}H_{28}N_2O_5/HCl \cdot 2.7H_2O$: C, 54.42; H, 7.14; N, 5.77.

Found: C, 54.31; H, 6.77; N, 5.92.

EXAMPLE 17

N-Hydroxy-N-[2-(3-(S)-hydroxypyrrolidin-1-yl)-1-(S)-phenylethyl]-2-(3-trifluoromethylphenyl) acetamide This was prepared from 2-(R)-phenyl-2-(3-(S)-tetrahydropyranyloxypyrrolidin-1-yl)ethanol and 3-trifluoromethylphenylacetic acid in 18.9% yield according to a procedure similar to that described in Preparation 4, Examples 10 and 11.

$^1$H NMR (270 MHz, CDCl$_3$) δ7.60–7.26 (9H, m), 5.75–5.65 (1H, m), 4.35–4.25 (1H, m), 3.99 (1H, d, J=14.3 Hz), 3.86 (1H, d, J=14.3 Hz), 3.54–3.38 (1H, m), 3.04–2.94 (1H, m), 2.84–2.40 (6H, m), 2.20–2.06 (1H, m), 1.70–1.55 (1H, m).

IR(neat): 3350, 1630 cm$^{-1}$.

MS m/z: 408(M+H)$^+$.

HCl salt: amorphous solid.

Anal. Calcd for $C_{21}H_{23}F_3N_2O_3 \cdot HCl \cdot 1.9H_2O$: C, 54.70; H, 5.64; N, 6.08. Found: C, 54.83; H, 5.97; N, 6.21.

EXAMPLE 18

N-Hydroxy-N-[2-(3-(S)-hydroxypyrrolidin-1-yl)-1-(S)-phenylethyl]-2-(4 -trifluoromethylphenyl) acetamide This was prepared from 2-(R)-phenyl-2-(3-(S)-tetrahydropyranyloxypyrrolidin-1-yl)ethanol and 4-trifluoromethylphenylacetic acid in 35.4% yield according to a procedure similar to that described in Preparation 4, Examples 10 and 11.

¹H NMR (270 MHz, CDCl₃) δ7.56 (2H, d, J=8.1 Hz), 7.44 (2H, d, J=8.1 Hz), 7.33–7.26 (5H, m), 5.65 (1H, dd, J=5.9, 11.0 Hz), 4.35–4.20 (1H, m), 3.99 (1H, d, J=14.3 Hz), 3.85 (1H, d, J=13.9 Hz), 3.41 (1H, dd, J=12.1, 12.5 Hz), 3.00–2.90 (1H, m), 2.82–2.02 (7H, m), 1.64–1.50 (1H, m).

IR(neat): 3100, 1650 cm⁻¹.

MS m/z: 408(M⁺).

HCl salt: mp 142.5–144.2° C.

Anal. Calcd for $C_{21}H_{23}F_3N_2O_3 \cdot HCl \cdot 0.2H_2O$: C, 56.24; H, 5.48; N, 6.25.

Found: C, 56.27; H, 5.61; N, 6.08.

EXAMPLE 19

2-(4-Biphenyl)-N-hydroxy-N-[2-(3-(S)-hydroxypyrrolidin-1-yl)-1-(S)-phenylethyl] acetamide This was prepared from 2-(R)-phenyl-2-(3-(S)-tetrahydropyranyloxypyrrolidin-1-yl)ethanol and 4-biphenylacetic acid in 38.8% yield according to a procedure similar to that described in Preparation 4, Examples 10 and 11.

¹H NMR (270 MHz, CDCl₃) δ7.60–7.26 (14H, m), 5.66 (1H, dd, J=5.1, 11.0 Hz), 4.20–4.14 (1H, m), 4.04 (1H, d, J=13.6 Hz), 3.76 (1H, d, J=13.2 Hz), 3.35 (1H, dd, J=10.3, 13.6 Hz), 2.90–2.80 (1H, m), 2.73–2.63 (2H, m), 2.55–2.45 (1H, m), 2.35–2.22 (1H, m), 2.10–1.96 (1H, m), 1.90 (2H, br.s), 1.50–1.35 (1H, m).

MS m/z: 417(M+H)⁺.

HCl salt: mp 163.8–165.5° C.

Anal. Calcd for $C_{26}H_{28}N_2O_3 \cdot HCl \cdot 0.5H_2O$: C, 67.60; H, 6.55; N, 6.06.

Found: C, 67.77; H, 6.42; N, 5.76.

EXAMPLE 20

N-Hydroxy-N-[2-(3-(S)-hydroxypyrrolidin-1-yl)-1-(S)-phenylethyl]-2-(4-nitrophenyl)acetamide This was prepared from 2-(R)-phenyl-2-(3-(S)-tetrahydropyranyloxypyrrolidin-1-yl)ethanol and 4-nitrophenylacetic acid in 11.6% yield according to a procedure similar to that described in Preparation 4, Examples 10 and 11.

¹H NMR (270 MHz, CDCl₃) δ8.14 (2H, d, J=8.8 Hz), 7.44 (2H, d, J=8.8 Hz), 7.35–7.16 (5H, m), 5.74 (1H, dd, J=4.8, 10.3 Hz), 4.46–4.38 (1H, m), 4.03 (1H, d, J=15.0 Hz), 3.96 (1H, d, J=15.0 Hz), 3.64–3.50 (1H, m), 3.20–3.10 (1H, m), 2.96 (1H, br.d), J=10.3 Hz), 2.90–2.74 (3H, m), 2.66 (2H, br.s), 2.30–2.16 (1H, m), 1.84–1.70 (1H, m).

IR(neat): 3400, 1630 cm⁻¹.

MS m/z: 385(M⁺).

HCl salt: amorphous solid.

Anal. Calcd for $C_{20}H_{23}N_3O_3 \cdot HCl \cdot 1.5H_2O$: C, 53.51; H, 6.06; N, 9.36.

Found: C, 53.71; H, 6.01; N, 9.11.

EXAMPLE 21

N-Hydroxy-N-[2-(3-(S)-hydroxypyrrolidin-1yl)-1-(S)-phenylethyl]-2-(3-nitrophenyl)acetamide This was prepared from 2-(R)-phenyl-2-(3-(S)-tetrahydropyranyloxypyrrolidin-1-yl)ethanol and 3-nitrophenylacetic acid in 11.6% yield according to a procedure similar to that described in Preparation 4, Examples 10 and 11.

¹H NMR (270 MHz, CDCl₃) δ8.17–8.08 (2H, m), 7.66–7.20 (7H, m), 5.64 (1H, dd, J=5.9, 11.0 Hz), 4.38–4.30 (1H, m), 4.03 (1H, d, J=14.7 Hz), 3.90, (1H, d, J=14.3 Hz), 3.50–3.38 (1H, m), 3.06–2.94 (1H, m), 2.84–2.70 (2H, m), 2.66–2.56 (1H, m), 2.50–2.32 (1H, m), 2.20–2.04 (1H, m), 1.96 (2H, br.s), 1.70–1.50 (1H, m).

MS (m/z: 386(M+H)⁺.

HCl salt: mp 154.3–155.5° C.

Anal. Calcd for $C_{20}H_{23}N_3O_5 \cdot HCl \cdot 0.3H_2O$: C, 56.22; H, 5.80; N, 9.83.

Found: C, 56.29; H, 5.80; N, 9.55.

EXAMPLE 22

2-(4-Chlorophenyl)-N-hydroxy-N-[2-(3-(S)-hydroxypyrrolidin-1-yl)-1-(S)-phenylethyl] acetamide This was prepared from 2-(R)-phenyl-2-(3-(S)-tetrahydropyranyloxypyrrolidin-1-yl)ethanol and 4-chlorophenylacetic acid in 49.4% yield according to a procedure similar to that described in Preparation 4, Examples 10 and 11.

¹H NMR (270 MHz, CDCl₃) δ7.40–7.20 (9H, m), 5.65 (1H, dd, J=5.1, 11.0 Hz), 5.00–3.30 (2H, wide spread br.s), 4.35–4.25 (1H, m), 3.86 (1H, d, J=13.9 Hz), 3.74 (1H, d, J=13.9 Hz), 3.40 (1H, dd, J=11.7, 12.1 Hz), 3.02–2.90 (1H, m), 2.75 (1H, br.d, J=10.6 Hz), 2.61 (1H, dd, J=5.1, 12.5 Hz), 2.51 (1H, dd, J=5.1, 10.3 Hz), 2.40–2.25 (1H, m), 2.23–2.08 (1H, m), 1.65–1.50 (1H, m).

IR(neat): 3400, 1630 cm⁻¹.

MS m/z: 374(M+).

HCl salt: mp 146.5–147.3° C.

Anal. Calcd for $C_{20}H_{23}ClN_2O_3 \cdot HCl \cdot 0.3H_2O$: C, 57.64; H, 5.95; N, 6.72.

Found: C, 57.87; H, 5.88; N, 6.78.

EXAMPLE 23

2-(3-Chlorophenyl)-N-hydroxy-N-[2-(3-(S)-hydroxypyrrolidin-1yl)-1-(S)-phenylethyl]acetamide This was prepared from 2-(R)-phenyl-2-(3-(S)-tetrahydropyranyloxypyrrolidin-1-yl)ethanol and 3-chlorophenylacetic acid in 29.6% yield according to a procedure similar to that described in Preparation 4, Examples 10 and 11.

¹H NMR (270 MHz, CDCl₃) δ7.34–7.20 (9H, m), 5.75–5.62 (1H, m), 4.35–4.25 (1H, m), 3.94 (1H, d, J=13.9 Hz), 3.74 (1H, d, J=13.9 Hz), 3.45 (1H, dd, J=9.5, 12.1 Hz), 3.05–2.92 (1H, m), 2.80 (1H, br.d, J=10.6 Hz), 2.77–2.30 (3H, m), 3.80–2.30 (2H, almost flat peak), 2.23–2.06 (1H, m), 1.68–1.54 (1H, m).

IR(neat): 3350, 1630 cm⁻¹.

MS m/z: 374(M⁺).

HCl salt: mp 113.2–114.3° C.

Anal. Calcd for $C_{20}H_{23}ClN_2O_3 \cdot HCl \cdot 0.4H_2O$: C, 57.40; H, 5.97; N, 6.69.

Found: C, 57.79; H, 5.84; N, 6.74.

EXAMPLE 24

2-(2-Chlorophenyl)-N-hydroxy-N-[2-(3-(S)-hydroxypyrrolidin-1-yl)-1-(S)-phenylethyl] acetamide This was prepared from 2-(R)-phenyl-2-(3-(S)-tetrahydropyranyloxypyrrolidin-1-yl)ethanol and 2-chlorophenylacetic acid in 31.2% yield according to a procedure similar to that described in Preparation 4, Examples 10 and 11.
$^1$H NMR (270 MHz, CDCl$_3$) δ7.45–7.16 (9H, m), 5.85–5.70 (1H, m), 4.44–4.34 (1H, m), 4.14 (1H, d, J=16.1 Hz), 3.91 (1H, d, J=16.1 Hz), 3.68–3.48 (1H, m), 3.24–3.10 (1H, m), 2.98–2.40 (6H, m), 2.34–2.18 (1H, m), 1.86–1.70 (1H, m).
IR(neat): 3400, 1640 cm$^{-1}$.
MS m/z: 374(M$^+$).
HCl salt: mp 146° C.
Anal. Calcd for C$_{20}$H$_{23}$ClN$_2$O$_3$.HCl.H$_2$O: C, 55.95; H, 6.10; N, 6.52.
Found: C, 56.18; H, 6.00; N, 6.55.

EXAMPLE 25

N-hydroxy-N-[2-(3-(S)-hydroxypyrrolidin-1-yl)-1-(S)-phenylethyl]-2-(2,3,5-trichlorophenyl)acetamide This was prepared from 2-(R)-phenyl-2-(3-(S)-tetrahydropyranyloxypyrrolidin-1-yl)ethanol and 2,3,5-trichlorophenylacetic acid in 51.6% yield according to a procedure similar to that described in Preparation 4, Examples 10 and 11.
$^1$H NMR (270 MHz, CDCl$_3$) δ7.45–7.26 (6H, m), 7.14 (1H, d, J=2.2 Hz), 5.70 (1H, dd, J=4.8, 11.0 Hz), 4.48–4.30 (1H, m), 4.20–3.00 (2H, wide spread br.s), 4.06 (1H, d, J=16.5 Hz), 3.90 (1H, d, J=16.1 Hz), 3.50 (1H, dd, J=11.4, 12.1 Hz), 3.20–3.10 (1H, m), 2.86 (1H, br.d, J=10.3 Hz), 2.75–2.60 (2H, m), 2.55–2.35 (1H, m), 2.35–2.20 (1H, m), 1.85–1.70 (1H, m).
IR(neat): 3400, 1640 cm$^{-1}$.
MS m/z: 444(M$^+$).
HCl salt: amorphous solid.
Anal. Calcd for C$_{20}$H$_{21}$Cl$_3$N$_2$O$_3$.HCl.H$_2$O: C, 48.21; H, 4.86; N, 5.62.
Found: C, 48.56; H, 5.17; N, 5.40.

EXAMPLE 26

N-Hydroxy-N-[2-(3-(S)-hydroxypyrrolidin-1-yl)-1-(S)-phenylethyl]-2-(2,4,6-trichlorophenyl)acetamide This was prepared from 2-(R)-phenyl-2-(3-(S)-tetrahydropyranyloxypyrrolidin-1-yl)ethanol and 2,4,6-trichlorophenylacetic acid in 14.0% yield according to a procedure similar to that described in Preparation 4, Examples 10 and 11.
$^1$H NMR (270 MHz, CDCl$_3$) δ7.50–7.26 (7H, m), 5.60 (1H, dd, J=4.8, 11.4 Hz), 4.47–4.38 (1H, m), 4.19 (2H, s), 3.49 (1H, dd, J=11.7, 12.1 Hz), 3.25–3.10 (1H, m), 2.84 (1H, br.d, J=9.5 Hz), 2.75–2.60 (2H, m), 2.50–2.35 (2H, m), 2.35–2.20 (2H, m), 1.90–1.70 (1H, m).
IR(KBr): 3450, 1640 cm-1.
MS m/z: 442(M+).
HCl salt: amorphous solid
Anal. Calcd for C$_{20}$H$_{21}$Cl$_3$N$_2$O$_3$.HCl.0.2H$_2$O: C, 49.65; H, 4.67; N, 5.79.
Found: C, 49.42; H, 4.39; N, 5.96.

EXAMPLE 27

N-Hydroxy-N-[2-(3-(S)-hydroxypyrrolidin-1-yl)-1-(S)-phenylethyl]-2-(2,4,6-trimentylphenyl)acetamide This was prepared from 2-(R)-phenyl-2-(3-(S)-tetrahydropyranyloxypyrrolidin-1-yl)ethanol and 2,4,6-trimethylphenylacetic acid in 67.8% yield according to a procedure similar to that described in Preparation 4, Examples 10 and 11.
$^1$H NMR (270 MHz, CDCl$_3$) δ7.45–7.25 (5H, m), 6.81 (2H, s), 5.80–5.65 (1H, m), 4.40–4.30 (1H, m), 3.86 (2H, s) 3.49 (1H, dd, J=11.7, 13.2 Hz), 3.20–3.10 (1H, m), 2.80 (1H, br.d, J=10.3 Hz), 2.65–2.50 (2H, m), 2.35–2.25 (3H, m), 2.23 (3H, s), 2.18 (6H, s), 1.90–1.65 (1H, m), 1.65–1.50 (1H, m).
IR(neat): 3250, 1630 cm$^{-1}$.
MS m/z: 382(M$^+$).
HCl salt: amorphous solid.
Anal. Calcd for C$_{23}$H$_{30}$N$_2$O$_3$.HCl.0.2H2O: C, 64.01; H, 7.57; N, 6.49.
Found: C, 64.08; H, 7.85; N, 6.61.

EXAMPLE 28

2-(2,3-Dichlorophenyl)-N-hydroxy-N-[2-(3-(S)-hydroxypyrrolidin-1-yl)-1-(S)-phenylethyl]acetamide This was prepared from 2-(R)-phenyl-2-(3-(S)-tetrahydropyranyloxypyrrolidin-1-yl)ethanol and 2-dichlorophenylacetic acid in 56% yield according to a procedure similar to that described in Preparation 4, Examples 10 and 11.
$^1$H NMR (270 MHz, CDCl$_3$) δ7.50–7.05 (8H, m), 5.69 (1H, dd, J=5.1, 11.4 Hz), 5.00–3.00 (2H, almost flat br.s), 4.45–4.35 (1H, m), 4.10 (1H, d, J=16.1 Hz), 3.92 (1H, d, J=16.1 Hz), 3.48 (1H, dd, J=11.7, 12.1 Hz), 3.20–3.10 (1H, m), 2.82 (1H, d, J=10.3 Hz), 2.70–2.55 (2H, m), 2.45–2.20 (2H, m), 1.80–1.70 (1H, m).
IR(neat): 3200, 1640 cm$^{-1}$.
MS m/z: 408(M+).
HCl salt: mp 155.3–158.1° C.
Anal. Calcd for C$_{20}$H$_{22}$Cl$_2$N$_2$O$_3$.HCl: C, 53.89; H, 5.20; N, 6.28.
Found: C, 53.72; H, 5.24; N, 6.16.

EXAMPLE 29

2-(2,4-Dichlorophenyl)-N-hydroxy-N-[2-(3-(S)-hydroxypyrrolidin-1-yl)-1-(S)-phenylethyl]acetamide This was prepared from 2-(R)-phenyl-2-(3-(S)-tetrahydropyranyloxypyrrolidin-1-yl)ethanol and 2,4-dichlorophenylacetic acid in 71.9% yield according to a procedure similar to that described in Preparation 4, Examples 10 and 11.
$^1$H NMR (270 MHz, CDCl$_3$) δ7.45–7.15 (8H, m), 5.69 (1H, dd, J=5.1, 11.4 Hz), 6.50–4.50 (2H, almost flat br.s), 4.35–4.25 (1H, m), 4.00 (1H, d, J=16.1 Hz), 3.86 (1H, d, J=16.1 Hz), 3.47 (1H, dd, J=11.7, 12.1 Hz), 3.20–3.10 (1H, m), 2.83 (1H, d, J=10.6 Hz); 2.61 (2H, dd, J=5.5, 12.1 Hz), 2.45–2.20 (2H, m), 1.80–1.65 (1H, m).
IR(neat): 3200, 1635 cm$^{-1}$.
MS m/z: 408(M$^+$).
HCl salt: mp 149–151.5° C.
Anal. Calcd for C$_{20}$H$_{22}$Cl$_2$N$_2$O$_3$.HCl.0.2H$_2$O: C, 53.46; H, 5.25; N, 6.23.
Found: C, 53.46; H, 5.19; N, 6.19.

EXAMPLE 30

2-(2,5-Dichlorophenyl)-N-hydroxy-N-[2-(3-(S)-hydroxypyrrolidin-1-yl)-1-(S)-phenylethyl]acetamide This was prepared from 2-(R)-phenyl-2-(3-(S)-tetrahydropyranyloxypyrrolidin-1-yl)ethanol and 2,5-dichlorophenylacetic acid in 56.3% yield according to a procedure similar to that described in Preparation 4, Examples 10 and 11.

$^1$H NMR (270 MHz, CDCl$_3$) δ7.45–7.15 (8H, m), 5.69 (1H, dd, J=5.1, 11.0 Hz), 5.60–4.50 (2H, almost flat br.s), 4.35–4.25 (1H, m), 4.03 (1H, d, J=16.1 Hz), 3.86 (1H, d, J=16.1 Hz), 3.47 (1H, t, J=11.7 Hz), 3.20–3.10 (1H, m), 2.82 (1H, d, J=10.6 Hz), 2.63 (2H, dd, J=5.1, 12.1 Hz), 2.45–2.20 (2H, m), 1.85–1.70 (1H, m).
IR(neat): 3200, 1635 cm$^{-1}$.
MS m/z: 408(M$^+$).
HCl salt: 157.5–158.2° C.
Anal. Calcd for C$_{20}$H$_{22}$Cl$_2$N$_2$O$_3$.HCl.0.2H$_2$O: C, 53.46; H, 5.25; N, 6.23.
Found: C, 53.35; H, 5.21; N, 6.14.

Preparation 7

2-(3-(S)-Methoxymethyloxypyrrolidin-1-yl)-2-(R)-phenylethanol

To a stirred solution of (S)-(–)-butanetriol (10.61 g, 0.1 mol) in pyridine (50 ml) was added p-toluenesulfonyl chloride (38.13 g, 0.2 mol) by portions at 0° C. (ice bath). After 1 h stirring, the reaction mixture was poured into c-HCl aqueous solution including ice and acidified to pH2. The mixture was extracted with ethyl acetate (100 ml×3). The extract combined was washed with brine, dried (Na$_2$SO$_4$), and concentrated to give 36.22 g of pale brown clear oil. To a stirred solution of this crude ditosylate (36.22 g) and methylal (50 ml) in CH$_2$Cl$_2$ (50 ml) was added P$_2$O$_5$ (20 g). After 1 h stirring, another 10 g of P$_2$O$_5$ was added to the reaction mixture. After 2 h stirring, the CH$_2$Cl$_2$ layer was separated. Residual dark brown solid was washed with CH$_2$Cl$_2$. The combined CH$_2$Cl$_2$ layer was washed with NaHCO$_3$ aqueous solution, dried (Na$_2$SO$_4$), and concentrated to give 38.51 g of brown viscous oil. A mixture of this oil (38.51 g, 84 mmol), (R)-(–)-2-phenylglycinol (10.97 g, 80 mmol), and triethylamine (23 mmol, 160 mmol) in ethanol (40 ml) was refluxed with stirring for 15 h. The solvent was evaporated and the residue was dissolved in CH$_2$Cl$_2$ (200 ml), washed with NaHCO$_3$ aqueous solution and brine, dried (Na$_2$SO$_4$), and concentrated to give 28.43 g of brown viscous oil. This oil was purified by column chromatography (silica gel 200 g, CH$_2$Cl$_2$/methanol: 40/1 to 20/1) to afford 9.74 g (48.4%) of clear brown visous oil.

$^1$H NMR (270 MHz, CDCl$_3$) δ7.40–7.25 (5H, m), 4.62 (1H, d, J=7.0 Hz), 4.58 (1H, d, J=6.6 Hz), 4.26–4.18 (1H, m), 3.92 (1H, dd, J=6.2, 11.0 Hz), 3.82 (1H, dd, J=5.5, 11.0 Hz), 3.54 (2H, t, J=5.9 Hz), 3.33 (3H, s), 2.93 (1H, br.s), 2.85–2.66 (3H, m), 2.56–2.47 (1H, m), 2.16–2.02 (1H, m), 1.88–1.77 (1H, m).

EXAMPLE 31

2-(2,6-Dichlorophenyl)-N-hydroxy-N-[2-(3-(S)-hydroxypyrrolidin-1-yl)-1-(S)-phenylethyl]acetamide This was prepared from 2-(3-(S)-methoxymethyloxypyrrolidin-1-yl)-2-(R)-phenylethanol and 2,6-dichlorophenylacetic acid in 47.2% yield according to a procedure similar to that described in Preparation 4, Examples 10 and 11.

$^1$H NMR (270 MHz, CDCl$_3$) δ750–7.25 (7H, m), 7.20–7.10 (1H, m), 5.71 (1H, dd, J=5.1, 11.4 Hz), 5.40–3.70 (2H, almost flat br.s), 4.50–4.40 (1H, m), 4.25 (2H, s), 3.50 (1H, dd, J=11.0, 12.5 Hz), 3.28–3.15 (1H, m), 2.87 (1H, d, J=10.3 Hz), 2.75–2.55 (2H, m), 2.50–2.25 (2H, m), 1.90–1.70 (1H, m).

IR(KBr): 3400, 1640 cm$^{-1}$.
MS m/z: 408(M$^+$).
HCl salt: 95.5–96.8° C.
Anal. Calcd for C$_{20}$H$_{22}$Cl$_2$N$_2$O$_3$.HCl.0.5H$_2$O: C, 52.82; H, 5.35 N, 6.16.
Found: C, 52.61; H, 5.13; N, 6.10.

EXAMPLE 32

2-(3,5-Dichlorophenyl)-N-hydroxy-N-[2-(3-(S)-hydroxypyrrolidin-1-yl)-1-(S)-phenylethyl]acetamide This was prepared from 2-(3-(S)-methoxymethyloxypyrrolidin-1-yl)-2-(R)-phenylethanol and 3,5-dichlorophenylacetic acid in 47.8% yield according to a procedure similar to that described in Preparation 4, Examples 10 and 11.

$^1$H NMR (270 MHz, CDCl$_3$) δ7.45–7.15 (8H, m), 5.63 (1H, dd, J=5.5, 11.0 Hz), 4.50–3.00 (2H, almost flat br.s), 4.40–4.28 (1H, m), 3.87 (1H, d, J=14.3 Hz), 3.71 (1H, d, J=14.3 Hz), 3.39 (1H, dd, J=11.4, 12.1 Hz), 3.05–2.95 (1H, m), 2.74 (1H, d, J=11.0 Hz), 2.65 (1H, dd, J=5.5, 12.5 Hz), 2.54 (1H, dd, J=5.5, 10.6 Hz), 2.45–2.30 (1H, m), 2.25–2.10 (1H, m), 1.70–1.55 (1H, m).
IR(neat): 3350, 1650 cm$^{-1}$.
MS m/z: 408(M$^+$).
HCl salt: amorphous solid.
Anal. Calcd for C$_{20}$H$_{22}$Cl$_2$N$_2$O$_3$.HCl.2H$_2$O: C, 49.86; H, 5.65; N, 5.81.
Found: C, 49.49; H, 5.53; N, 5.59.

EXAMPLE 33

N-Hydroxy-N-[2-(3-(S)-hydroxypyrrolidin-1-yl)-1-(S)-phenylethyl]-2-(2,3,6-trichlorophenyl)acetamide This was prepared from 2-(3-(S)-methoxymethyloxypyrrolidin-1-yl)-2-(R)-phenylethanol and 2,3,6-trichlorophenylacetic acid in 46.7% yield according to a procedure similar to that described in Preparation 4, Examples 10 and 11.

$^1$H NMR (270 MHz, CDCl$_3$) δ7.45–7.20 (7H, m), 5.69 (1H, dd, J=4.8, 11.0 Hz), 5.00–3.50 (2H, almost flat br.s), 4.50–4.40 (1H, m), 4.29 (2H, s), 3.49 (1H, t, J=11.7 Hz), 3.25–3.15 (1H, m), 2.85 (1H, d, J=10.3 Hz), 2.70–2.60 (2H, m), 2.45–2.20 (2H, m), 1.90–1.70 (1H, m).
IR(KBr): 3400, 1640 cm$^{-1}$.
MS m/z: 442(M$^+$).
HCl salt: 102–103° C.
Anal. Calcd for C$_{20}$H$_{21}$Cl$_3$N$_2$O$_3$.HCl.H$_2$O: C, 48.21; H, 4.86; N, 5.62.
Found: C, 48.40; H, 4.64; N, 5.52.

EXAMPLE 34

2-(Benzo[b]furan-4-yl)-N-hydroxy-N-[2-(3-(S)-hydroxypyrrolidin-1-yl)-1-(S)-phenylethyl]acetamide This was prepared from 2-(3-(S)-methoxymethyloxypyrrolidin-1-yl)-2-(R)-phenylethanol and 4-benzo[b]furanacetic acid in 57.5% yield according to a procedure similar to that described in Preparation 4, Examples 10 and 11.

$^1$H NMR (270 MHz, CDCl$_3$) δ7.64 (1H, d, J=2.2 Hz), 7.50–7.25 (7H, m), 7.14 (1H, d, J=7.3 Hz), 6.84 (1H, dd, J=0.7, 2.2 Hz), 5.61 (1H, dd, J=5.5, 11.4 Hz), 4.24 (1H, d, J=13.6 Hz), 4.05–3.95 (1H, m), 3.91 (1H, d, J=13.2 Hz), 3.31 (1H, dd, J=11.7, 12.1 Hz), 2.75–2.65 (1H, m), 2.63–2.50 (2H, m), 2.30 (1H, dd, J=5.1, 10.3 Hz), 2.20–2.10 (1H, m), 2.00–1.85 (1H, m).
IR(neat): 3400, 1635 cm$^{-1}$.
MS m/z: 380(M$^+$).
HCl salt: amorphous solid.
Anal. Calcd for $C_{22}H_{24}N_2O_4 \cdot HCl \cdot 1.1H_2O$: C, 60.51; H, 6.28; N, 6.41.
Found: C, 60.31; H, 5.98; N, 6.47.

EXAMPLE 35

N-Hydroxy-N-[2-(3-(S)-hydroxypyrrolidin-1-yl)-1-(S)-phenylethyl]-2-(1-tetralon-6-yl)acetamide This was prepared from 2-(3-(S)-methoxymethyloxypyrrolidin-1-yl)-2-(R)-phenylethanol and (1-tetralon-6-yl)acetic acid in 59.4% yield according to a procedure similar to that described in Preparation 4, Examples 10 and 11.
$^1$H NMR (270 MHz, CDCl$_3$) δ7.96 (1H, d, J=8.1 Hz), 7.40–7.18 (7H, m), 5.66 (1H, dd, J=5.5, 11.0 Hz), 4.30–4.20 (1H, m), 3.94 (1H, d, J=14.3 Hz), 3.81 (1H, d, J=13.9 Hz), 3.80–2.00 (2H, almost flat br.s), 3.40 (1H, dd, J=11.7, 12.1 Hz), 3.00–2.85 (3H, m), 2.80–2.50 (5H, m), 2.45–2.30 (1H, m), 2.20–2.05 (3H, m), 1.65–1.50 (1H, m).
IR(neat): 3400, 1680, 1640 cm$^{-1}$.
MS m/z: 408(M$^+$).
HCl salt: amorphous solid.
Anal. Calcd for $C_{24}H_{28}N_2O_4 \cdot HCl \cdot 1.2H_2O$: C, 61.78; H, 6.78; N, 6.00.
Found: C, 61.60; H, 6.59; N, 6.35.

EXAMPLE 36

2-(3,4-Dimethylphenyl)-N-hydroxy-N-[2-(3-(S)-hydroxypyrrolidin-1-yl)-1-(S)-phenylethyl]acetamide This was prepared from 2-(3-(S)-methoxymethyloxypyrrolidin-1-yl)-2-(R)-phenylethanol and 3,4-dimethylphenylacetic acid in 66.8% yield according to a procedure similar to that described in Preparation 4, Examples 10 and 11.
$^1$H NMR (270 MHz, CDCl$_3$) δ7.45–7.25 (5H, m), 7.20–7.00 (3H, m), 5.66 (1H, dd, J=5.1, 11.4 Hz), 4.25–4.10 (1H, m), 3.87 (1H, d, J=13.9 Hz), 3.67 (1H, d, J=13.9 Hz), 3.37 (1H, dd, J=11.7, 12.1 Hz), 3.00–2.85 (1H, m), 2.71 (1H, d, J=9.9 Hz), 2.55 (1H, dd, J=5.5, 12.5 Hz), 2.42 (1H, dd, J=5.1, 9.9 Hz), 2.35–2.05 (9H, m, including each 3H, s, at 2.22 and 2.21 ppm), 1.80–1.35 (2H, m).
IR(neat): 3350, 1630 cm$^{-1}$.
MS m/z: 368(M$^+$).
HCl salt: amorphous solid.
Anal. Calcd for $C_{22}H_{28}N_2O_3 \cdot HCl \cdot 1.8H_2O$: C, 60.42; H, 7.51; N, 6.41.
Found: C, 60.51; H, 7.71; N, 6.29.

EXAMPLE 37

2-(3,4-Dichlorophenyl)-N-hydroxy-N-[2-(3-(S)-hydroxypyrrolidin-1-yl)-1-(R)-phenylethyl]acetamide This was prepared from 2-(3-(S)-methoxymethyloxypyrrolidin-1-yl)-2-(S)-phenylethanol and 3,4-dichlorophenylacetic acid in 32.8% yield according to a procedure similar to that described in Preparation 4, Examples 10 and 11.
$^1$H NMR (270 MHz, CDCl$_3$) δ7.45–7.25 (7H, m), 7.13 (1H, dd, J=1.5, 8.1 Hz), 5.61 (1H, dd, J=5.5, 10.6 Hz), 5.00–3.90 (2H, almost flat br.s), 4.45–4.35 (1H, m), 3.85 (1H, d, J=14.7 Hz), 3.77 (1H, d, J=14.3 Hz), 3.37 (1H, dd, J=11.0, 12.5 Hz), 2.89 (1H, dd, J=4.7, 8.4 Hz), 280–2.60 (3H, m), 2.45–2.35 (1H, m), 2.15–2.00 (1H, m), 1.80–1.65 (1H, m).
IR(KBr): 3450, 3250, 1650 cm$^{-1}$.
MS m/z: 408(M$^+$).
HCl salt: 125.5–126.0° C.
[α]D=−95.4° (c=0.218, methanol)
Anal. Calcd for $C_{20}H_{22}Cl_2N_2O_3$: C, 58.69; H, 5.42 N, 6.84.
Found: C, 58.51; H, 5.42; N, 6.70.

EXAMPLE 38

2-(3,4-Difluorophenyl)-N-hydroxy-N-[2-(3-(S)-hydroxypyrrolidin-1-yl)-1-(S)-phenylethyl]acetamide This was prepared from 2-(3-(S)-methoxymethyloxypyrrolidin-1-yl)-2-(R)-phenylethanol and 3,4-diflourophenylacetic acid in 53.6% yield according to a procedure similar to that described in Preparation 4, Examples 10 and 11.
$^1$H NMR (270 MHz, CDCl$_3$) δ7.40–7.25 (5H, m), 7.18–6.95 (3H, m), 5.65 (1H, dd, J=5.5, 11.4 Hz), 5.00–3.90 (2H, almost flat br.s), 4.35–4.25 (1H, m), 3.82 (1H, d, J=14.3 Hz), 3.74 (1H, d, J=14.3 Hz), 3.40 (1H, dd, J=10.6, 13.2 Hz), 2.95 (1H, dt, J=4.4, 8.8 Hz), 2.75 (1H, d, J=10.6 Hz), 2.61 (1H, dd, J=5.1, 12.5 Hz), 2.51 (1H, dd, J=5.5, 10.6 Hz), 2.40–2.10 (2H, m), 1.70–1.50 (1H, m).
IR(neat): 3350, 3250, 1630 cm$^{-1}$.
MS m/z: 376(M$^+$).
HCl salt: amorphous solid.
Anal. Calcd for $C_{20}H_{22}F_2N_2O_3 \cdot HCl \cdot 0.5H_2O$: C, 56.94; H, 5.73; N, 6.64.
Found: C, 57.21; H, 6.07; N, 6.63.

EXAMPLE 39

2-(Benzo[b]thiophen-4-yl)-N-hydroxy-N-[2-(3-(S)-hydroxypyrrolidin-1-yl)-1-(S)-phenylethyl]acetamide This was prepared from 2-(3-(S)-methoxymethyloxypyrrolidin-1-yl)-2-(R)-phenylethanol and (benzo[b]thiophen-4-yl)acetic acid in 48.8% yield according to a procedure similar to that described in Preparation 4, Examples 10 and 11.
$^1$H NMR (270 MHz, CDCl$_3$) δ7.79 (1H, d, J=7.7 Hz), 7.66 (1H, d, J=5.5 Hz), 7.50–7.20 (8H, m), 5.60 (1H, dd, J=5.5, 11.4 Hz), 4.60–3.20 (2H, almost flat br.s), 4.32 (1H, d, J=13.6 Hz), 4.01 (1H, d, J=13.6 Hz), 4.00–3.90 (1H, m), 3.30 (1H, dd, J=11.7, 12.1 Hz), 2.70–2.45 (3H, m), 2.28 (1H, dd, J=5.1, 10.3 Hz), 2.20–2.10 (1H, m), 1.95–1.80 (1H, m), 1.20–1.05 (1H, m).
IR(neat): 3400, 3200, 1630 cm$^{-1}$.
MS m/z: 396(M$^+$).
HCl salt: amorphous solid.
Anal. Calcd for $C_{22}H_{24}N_2O_3S \cdot HCl \cdot 0.5H_2O$: C, 59.79; H, 5.93; N, 6.34.
Found: C, 59.85; H, 6.09; N, 6.27.

EXAMPLE 40

N-hydroxy-N-[2-(3-(S)-hydroxypyrrolidin-1-yl)-1-(S)-phenylethyl]-2-(3,4-methylenedioxyphenyl)acetamide This was prepared from 2-(3-(S)-methoxymethyloxypyrrolidin-1-yl)-2-(R)-phenylethanol and 3,4-methylenedioxyphenylacetic acid in 59.7% yield according to a procedure similar to that described in Preparation 4, Examples 10 and 11.
$^1$H NMR (270 MHz, CDCl$_3$) δ7.45–7.25 (5H, m), 6.85–6.70 (3H, m), 5.92 (2H, s), 5.66 (1H, dd, J=5.5, 11.4 Hz), 4.50–3.30 (2H, almost flat br.s), 4.30–4.20 (1H, m), 3.86 (1H, d, J=13.6 Hz), 3.64 (1H, d, J=13.9 Hz), 3.39 (1H, t, J=12.1 Hz), 3.05–2.95 (1H, m), 2.72 (1H, d, J=10.3 Hz), 2.59 (1H, dd, J=5.5, 12.5 Hz), 2.48 (1H, dd, J=5.5, 10.3 Hz), 2.35–2.10 (2H, m), 1.65–1.50 (1H, m).
IR(neat): 3400, 3250, 1630 cm$^{-1}$.
MS m/z: 384(M$^+$).
HCl salt: amorphous solid.
Anal. Calcd for C$_{21}$H$_{24}$N$_2$O$_5$·HCl·1.4H$_2$O: C, 56.54; H, 6.28; N, 6.28.
Found: C, 56.74; H, 6.38; N, 5.89.

EXAMPLE 41

2-(3,5-Difluorophenyl)-N-hydroxy-N-[2-(3-(S)-hydroxypyrrolidin-1-yl)-1-(S)-phenylethyl] acetamide This was prepared from 2-(3-(S)-methoxymethyloxypyrrolidin-1-yl)-2-(R)-phenylethanol and 3,4-diflourophenylacetic acid in 40.0% yield according to a procedure similar to that described in Preparation 4, Examples 10 and 11.
$^1$H NMR (270 MHz, CDCl$_3$) δ7.40–7.25 (5H, m), 6.82 (2H, d, J=8.1 Hz), 6.72–6.64 (1H, m), 5.65 (1H, dd, J=5.1, 11.0 Hz), 5.30–4.20 (2H, almost flat br.s), 4.40–4.30 (1H, m), 3.86 (1H, d, J=14.3 Hz), 3.74 (1H, d, J=14.3 Hz), 3.41 (1H, dd, J=11.7, 12.1 Hz), 3.10–2.95 (1H, m), 2.76 (1H, d, J=10.6 Hz), 2.61 (1H, dd, J=5.1, 12.5 Hz), 2.52 (1H, dd, J=5.5, 10.6 Hz), 2.40–2.10 (2H, m), 1.70–1.55 (1H, m).
IR(neat): 3350, 3200, 1630 cm$^{-1}$.
MS m/z: 376(M$^+$).
HCl salt: amorphous solid.
Anal. Calcd for C$_{20}$H$_{22}$F$_2$N$_2$O$_3$·HCl·0.5H$_2$O: C, 56.94; H, 5.73; N, 6.64.
Found: C, 57.01; H, 5.93; N, 6.45.

Preparation 8

1-Benzyl-3-(R)-tetrahydropyranyloxypyrrolidine

To a stirred solution of (R)-(+)-1-benzyl-3-pyrrolidinol (5.00 g, 28 mmol) and D-camphor-10-sulfonic acid (6.97 g, 30 mmol) in CH$_2$Cl$_2$ (10 ml) was added 3,4-dihydro-2H-pyran (20 ml) at rt and the reaction mixture was stirred for 14 h (in most cases, the reaction was completed after exothermic reaction subsided). The reaction mixture was diluted with CH$_2$Cl$_2$ (100 ml), washed with saturated NaHCO$_3$ aqueous solution, dried (Na$_2$SO$_4$), and concentrated to give brown oil. This was purified by column chromatography (silica gel: 200 g, CH$_2$Cl$_2$/MeOH: 40/1 as eluent) to give 8.78 g (97.6%) of desired compound as brown oil.
$^1$H NMR (270 MHz, CDCl$_3$) δ7.34–7.22 (5H, m) 4.61 (0.5H, dd, J=2.9, 4.4 Hz), 4.54 (0.5 H, dd, J=2.9, 4.4 Hz), 4.42–4.31 (1H, m) 3.90–3.79 (1H, m), 3.67 (1H, d, J=12.8 Hz), 3.59 (0.5H, d, J=12.8 Hz), 3.58 (0.5H, d, J=12.8 Hz), 3.50–3.40 (1H, m), 2.88 (0.5H, dd, J=6.6, 10.3 Hz), 2.74–2.45 (3.5H, m), 2.25–2.05 (1H, m), 1.95–1.45 (7H, m).

Preparation 9

3-(R)-Tetrahydropyranyloxypyrrolidine

A mixture of 1-benzyl-3-(R)-tetrahydropyranyloxypyrrolidine (8.78 g, 27.3 mmol) and Pearlman's catalyst (3.50 g) in MeOH (100 ml) was stirred under hydrogen atmosphere at rt for 4 h. After removal of the catalyst by Celite filtration, the filtrate was concentrated to give 5.74 g of clear light brown oil. This was used for the next reaction without purification.
$^1$H NMR (270 MHz, CDCl$_3$) δ4.62 (1H, br.s), 4.45–4.30 (1H, m), 3.90–3.80 (1H, m), 3.55–3.45 (1H, m), 3.20–2.80 (5H, m), 2.00–1.40 (8H, m).

Preparation 10

1-(S)-Phenyl-2-(3-(R)-tetrahydropyranyloxypyrrolidin-1-yl)ethanol and 2-(R)-Phenyl-2-(3-(R)-tetrahydropyranyloxypyrrolidin-1-yl)ethanol A mixture of 3-(R)-tetrahydropyranyloxypyrrolidine (1.43 g, 8.32 mmol) and (S)-(−)-styrene oxide (1.00 g, 8.32 mmol) in EtOH (10 ml) was refluxed with stirring for 1 h. Evaporation of the solvent gave 3.098 g of brown oil, which was purified by column chromatography (silica gel: 100 g, CH$_2$Cl$_2$/MeOH: 40/1 to 15/1 as eluent) to afford 1.68 g (69.3%) of clear light brown oil as about 2 to 1 mixture of title compounds in which 1-(S)-phenyl-2-(3-(R)-tetrahydropyranyloxypyrrolidin-1-yl)ethanol was main.
$^1$H NMR (270 MHz, CDCl$_3$) δ7.40–7.24 (5H, m), 4.72 and 4.68 (total 0.67H, app.each d, J=2.6 Hz, OCHO), 4.63–4.55 (1H, m, PhCHOH and OCHO), 4.43–4.25 (1H, m, OCHCH$_2$N), 3.89–3.81 (1.67H, m), 3.52–3.46 (1.33H, m), 2.88–2.47 (5.33H, m), 2.15–1.90 (2H, m), 1.86–1.66 (3H, m), 1.58–1.51 (4H, m).

EXAMPLE 42

2-(3,4-Dichlorophenyl)-N-[1-(S)-phenyl-2-(3-(R)-tetrahydropyranyloxypyrrolidin-1-yl)ethyl]-N-tetrahydropyranyloxyacetamide To a stirred solution of 1-(S)-phenyl-2-(3-(R)-tetrahydropyranyloxypyrrolidin-1-yl)ethanol (1.67 g, 5.73 mmol) and Et$_3$N (0.96 ml, 6.88 mmol) in CH$_2$Cl$_2$ (20 ml) was added dropwise mesyl chloride (0.53 ml, 6.88 mmol) at 0° C. The reaction mixture was stirred at rt for 16 h. The reaction mixture was washed with saturated NaHCO$_3$ aqueous solution and brine, dried (Na$_2$SO$_4$), and concentrated to give 2.02 g of brown oil. This oil was used for next reaction without purification.
$^1$H NMR (270 MHz, CDCl$_3$) δ7.42–7.30 (5H, m), 4.94 (1H, dd, J=5.9, 8.1 Hz, PhCHCl), 4.60 and 4.52 (total 1H, each m, OCHO), 4.35–4.31 (1H, m, OCHCH$_2$N), 3.88–3.82 (1H, m), 3.48–3.45 (1H, m), 3.25–3.17 (1H, m), 3.02–2.69 (3H, m), 2.66–2.50 (3H, m), 1.88–1.67 (3H, m), 1.56–1.51 (4H, m).

A mixture of crude chloride derivative (2.02 g, 5.73 mmol) and O-(tetrahydropyranyl)hydroxylamine (0.806 g, 6.88 mmol) in EtOH (10 ml) was refluxed with stirring for 0.5 h. The reaction mixture was concentrated, diluted with CH$_2$Cl$_2$ (30 ml), washed with saturated NaHCO$_3$ aqueous solution and brine, dried (Na$_2$SO$_4$), and concentrated to give 2.59 g of brown oil. This oil was used for the next reaction without purification.

A mixture of the above crude amine derivative (2.59 g, 5.73 mmol), 3,4-dichlorophenylacetic acid (1.41 g, 6.88 mmol), and 1-ethyl-3-(3-dimethylaminopropyl)carbodiimide hydrochloride (abbreviated as WSC, 1.32 g, 6.88 mmol) in CH$_2$Cl$_2$ (15 ml) was stirred at rt for 0.5 h. The reaction mixture was washed with saturated NaHCO$_3$ aqueous solution and brine, dried (Na$_2$SO$_4$), and concentrated to give 4.12 g of brown oil. This oil was purified by column

EXAMPLE 43

2(3,4-Dichlorophenyl)-N-hydroxy-N-[2-(3-(R)-hydroxypyrrolidin-1-yl)-1-(S)-phenylethyl] acetamide A mixture of above amide derivative (2.20 g, 3.81 mmol) and HCl gas containing MeOH (10 ml) was stirred at rt for 1 h. The reaction mixture was concentrated, basified with $NH_3$ aqueous solution, and extracted with $CH_2Cl_2$ (30 ml). The extract was washed with brine, dried ($Na_2SO_4$), and concentrated to give light brown powder. This was collected by filtration and washed with hexane to afford 1.117 g (71.6%) of light brown powder.
$^1$H NMR (270 MHz, $CDCl_3$) δ7.41–7.28 (7H, m), 7.13 (1H, dd, J=1.8, 8.4 Hz), 5.61 (1H, dd, J=5.5, 10.6 Hz), 4.50–3.50 (2H, almost flat br.s), 4.40–4.35 (1H, m), 3.84 (1H, d, J=14.7 Hz), 3.77 (1H, d, J=14.3 Hz), 3.38 (1H, dd, J=11.0, 12.1 Hz), 2.94–2.85 (1H, m), 2.74–2.63 (3H, m), 2.44–2.35 (1H, m), 2.15–2.01 (1H, m), 1.80–1.65 (1H, m). IR(KBr): 3250, 1650 $cm^{-1}$.
MS m/z: 408($M^+$).
HCl salt: amorphous solid.
Anal. Calcd for $C_{20}H_{22}Cl_2N_2O·HCl·0.8H_2O$: C, 52.20; H, 5.39; N, 6.09.
Found: C, 52.22; H, 5.39; N, 6.12.

EXAMPLE 44

2-(3,4-Dichlorophenyl)-N-hydroxy-N-[2-(3-(R)-hydroxypyrrolidin-1-yl)-1-(R)-phenylethyl] acetamide This was prepared from 3-(R)-tetrahydropyranyloxypyrrolidine and (R)-(+)-styrene oxide in 33.3% yield according to the procedure similar to that described in Examples 3 to 5.
$^1$H NMR (270 MHz, $CDCl_3$) δ7.38 (1H, d, J=8.4 Hz), 7.36–7.25 (6H, m), 7.13 (1H, dd, J=1.8, 8.1 Hz), 5.64 (1H, dd, J=5.1, 11.0 Hz), 5.00–3.50 (2H, almost flat br.s), 4.35–4.25 (1H, m), 3.84 (1H, d, J=14.3 Hz), 3.73 (1H, d, J=13.2 Hz), 3.40 (1H, dd, J=11.4, 12.5 Hz), 3.05–2.95 (1H, m), 2.74 (1H, br.d, J=10.3 Hz), 2.62 (1H, dd, J=5.1, 12.5 Hz), 2.51 (1H, dd, J=5.5, 10.6 Hz), 2.40–2.25 (1H, m) 2.25–2.10 (1H, m), 1.70–1.55 (1H, m).
IR(KBr): 3400, 3200, 1640 $cm^{-1}$.
MS m/z: 408($M^+$)
HCl salt: amorphous solid
Anal. Calcd for $C_{20}H_{22}Cl_2N_2O_3·HCl·0.5H_2O$: C, 52.82; H, 5.32; N, 6.16.
Found: C, 52.71; H, 5.59; N, 6.15

Preparation 11

(S)-1-(3-Methylphenyl)-1,2-ethanediol

A mixture of 3-methylstyrene (1.69 ml, 12.7 mmol), and AD-mix-α (17.78 g, 12.7 mmol) in water (65 ml) and t-BuOH (65 ml) was stirred at 0° C. for 3.5 h. To this reaction mixture was added $Na_2SO_3$ (20 g) and the mixture was stirred at rt for 1 h. The reaction mixture was extracted with ethyl acetate. The extract was washed with brine, dried ($Na_2SO_4$), and concentrated to give 2.07 g of light brown oil, which was purified by column chromatography (silica gel: 110 g, ethyl acetate/hexane: 3/2) to afford 1.89 g (98%) of desired product as light brown oil.
$^1$H NMR (270 MHz, $CDCl_3$) δ7.24 (1H, dd, J=7.3, 7.7 Hz), 7.19–7.09 (3H, m), 4.77 (1H, dd, J=3.7, 8.1 Hz), 3.74 (1H, dd, J=3.7, 11.4 Hz), 3.65 (1H, dd, J=8.1, 11.4 Hz), 2.82 (1H, br.s), 2.35 (3H, s), 1.77 (1H, br.s).

Preparation 12

(S)-1-(3-Methylphenyl)-1,2-ethanediol 2-tosylate

To a stirred solution of (S)-1-(3-methylphenyl)-1,2-ethanediol (1.78 g, 11.7 mmol) in pyridine (35 ml) was added p-toluenesulfonyl chloride (2.46 g, 12.9 mmol), and 4-dimethylaminopyridine (1.58 g, 12.9 mmol) at 0° C. and the reaction mixture was stirred at 0° C. to rt for 17 h. The reaction mixture was acidified with 6N HCl aqueous solution and extracted with $CH_2Cl_2$. The extract was washed with water and brine, dried ($Na_2SO_4$), and concentrated to give 3.02 g of yellow oil, which was purified by column chromatography (silica gel: 100 g, ethyl acetate/hexane: 1/9 to 1/3) to afford 2.63 g (73%) of desired product as light yellow oil. Its optical purity was 97% ee by HPLC employing a chiral stationary phase (chiral pak AS, Daicel Chemical Industries, eluted with n-hexane/EtOH: 98/2; detection time: 55 min for (R)-isomer 59 min for (S)-isomer).
$^1$H NMR (270 MHz, $CDCl_3$) δ7.77 (2H, d, J=8.4 Hz), 7.33 (2H, d, J=8.1 Hz), 7.22 (1H, dd, J=7.7, 8.1 Hz), 7.15–7.05 (3H, m), 4.94 (1H, ddd, J=2.9, 2.9, 8.4 Hz), 4.15 (1H, dd, J=2.9, 10.3 Hz), 4.04 (1H, dd, J=8.4, 10.3 Hz), 2.54 (1H, br.d, J=2.9 Hz), 2.45 (3H, s), 2.33 (3H, s), 1.58 (3H, s).

Preparation 13

2-(3-(S)-Methoxymethyloxypyrrolidin-1-yl)-1-(S)-(3-methylphenyl)-ethanol and 2-(3-(S)-methoxymethyloxypyrrolidin-1-yl)-2-(R)-(3-methylphenyl)ethanol A mixture of (S)-1-(3-methylphenyl)-1,2-ethanediol 2-tosylate (2.63 g, 8.59 mmol), (S)-3-methoxymethyloxypyrrolidine (1.24 g, 9.45 mmol), and $K_2CO_3$ (1.31 g, 9.45 mmol) in ethanol (25 ml) was refluxed with stirring for 2 h. After removal of the solvent by evaporation, the residue was diluted with water and extracted with $CH_2Cl_2$. The extract was washed with rine, dried ($Na_2SO_4$), and concentrated to give 2.11 g of brown oil, which was purified by column chromatography (silica gel: 110 g, $CH_2Cl_2$/MeOH: 15/1 to 10/1) to afford 1.72 g (76%) of 3 to 2 mixture of desired products as a light brown oil.
$^1$H NMR (270 MHz, $CDCl_3$) δ7.26–7.05 (4H, m), 4.68 (0.6H, dd, J=2.9, 10.6 Hz, PhCHOH), 4.67 (0.6H, d, J=7.0 Hz, $OCH_2O$), 4.63 (0.6H, d, J=6.6 Hz, $OCH_2O$), 4.62 (0.4H, d, J=7.0 Hz, $OCH_2O$), 4.59 (0.4H, d, J=7.0 Hz, $OCH_2O$), 4.34–4.24 (0.6H, m, $OCHCH_2N$), 4.24–4.16 (0.4H, m, $OCHCH_2N$), 3.88 (0.4H, dd, J=6.2, 10.6 Hz, $CHCH_2OH$), 3.79 (0.4H, dd, J=5.8, 11.0 Hz, $CHCH_2OH$), 3.47 (0.4H, dd, J=5.8, 6.2 Hz, NCHPh), 3.38 (1.8H, s), 3.33 (1.2H, s), 3.05–2.92 (1.2H, m), 2.82–2.40 (4H, m), 2.35 (3H, s), 2.25–1.50 (3H, m).

EXAMPLE 45

2-(3,4-Dichlorophenyl)-N-[2-(3-(S)-methoxymethyloxypyrrolidin-1-yl)-1-(S)-(3-methylphenyl)ethyl]-N-tetrahydropyranyloxyacetamide This was prepared from a mixture of 2-(3-(S)-methoxymethyloxypyrrolidine-1-yl)-1-(S)-(3- methylphenyl)ethanol and 2-(3-(S)-methoxymethyloxypyrrolidin-1-yl)-2-(R)-(3-methylphenyl)ethanol in 60% yield according to the procedure similar to that described in Example 4.

$^1$H NMR (270 MHz, CDCl$_3$) δ7.39 (0.5H, d, J=1.8 Hz), 7.35 (0.5H, d, J=8.4 Hz), 7.27–7.02 (5.5H, m), 6.96 (0.5H, dd, J=1.8, 8.4 Hz), 5.65 (0.5H, dd, J=5.1, 11.4 Hz, PhCHN), 5.52 (0.5H, dd, J=4.8, 11.0 Hz, PhCHN), 5.30–5.20 (1H, m, NOCHO), 4.64 (0.5H, d, J=6.6 Hz, OCH$_2$O), 4.63 (0.5H, d, J=7.0 Hz, OCH$_2$O), 4.61 (0.5H, d, J=6.6 Hz, OCH$_2$O), 4.60 (0.5H, d, J=6.6 Hz, OCH$_2$O), 4.30–4.20 (0.5H, m, OCHCH$_2$N), 4.20–4.10 (0.5H, m, OCHCH$_2$N), 4.06–3.85 (3H, m), 3.56–3.36 (1.5H, m), 3.35 (1.5H, s, OMe), 3.34 (1.5H, s, OMe), 3.24–3.10 (0.5H, m), 3.01–2.80 (2H, m), 2.66–2.40 (3H, m), 2.34 (1.5H, s), 2.28 (1.5H, s), 2.15–1.15 (8H, m).

EXAMPLE 46

2-(3,4-Dichlorophenyl)-N-hydroxy-N-[2-(3-(S)-hydroxypyrrolidin-1-yl)-1-(S)-(3-methylphenyl)ethyl]acetamide This was prepared from 2-(3,4-dichlorophenyl)-N-[2-(3-(S)-methoxymethyloxypyrrolidin-1-yl)-1-(S)-(3-methylphenyl)ethyl]-N-tetrahydropyranyloxyacetamide in 77% yield according to the procedure similar to that described in Example 5.

$^1$H NMR (270 MHz, CDCl$_3$) δ7.42–7.05 (7H, m), 5.59 (1H, dd, J=5.1, 11.0 Hz, PhCHN), 4.35–4.25 (1H, m, CHOH), 3.85 (1H, d, J=14.3 Hz, COCH$_2$Ph), 3.74 (1H, d, J=15.8 Hz, COCH$_2$Ph), 3.50–2.50 (2H, almost flat br.s, OH×2), 3.38 (1H, dd, J=11.7, 12.1 Hz), 3.00–2.90 (1H, m), 2.73 (1H, br.d, J=10.6 Hz), 2.62 (1H, dd, J=5.1, 12.5 Hz), 2.53 (1H, dd, J=5.5, 10.6 Hz), 2.40 –2.25 (4H, m, including 3H, s at 2.30 ppm), 2.23–2.07 (1H, m), 1.65–1.55 (1H, m).
IR(neat): 3350, 1650 cm$^{-1}$.
MS m/z: 422(M$^+$)
HCl salt: amorphous solid
Anal. Calcd for C$_{21}$H$_{24}$Cl$_2$N$_2$O$_3$.HCl.1.5H$_2$O: C, 51.81; H, 5.80; N, 5.75.
Found: C, 51.85; H, 5.72; N, 5.74.

EXAMPLE 47

N-[1-(S)-(4-Chlorophenyl)-2-(3-(S)-hydroxypyrrolidin-1-yl)ethyl]-2-(3,4-dichlorophenyl)-N-hydroxyacetamide This was prepared from 4-chlorostyrene and 3-(S)-methoxymethyloxypyrrolidine in 12% overall yield according to a procedure similar to that described in Examples 7 to 11.

$^1$H NMR (CDCl$_3$) δ7.40 (1H, d, J=2.2 Hz), 7.36 (1H, d, J=8.4 Hz), 7.30–7.20 (4H, m), 7.14 (1H, dd, J=2.2, 8.1 Hz), 5.58 (1H, dd, J=5.1, 11.0 Hz, PhCHN), 5.00–3.00 (2H, almost flat br.s, OH×2), 4.35–4.25 (1H, m, CHOH), 3.85 (1H, d, J=14.3 Hz, COCH$_2$Ph), 3.72 (1H, d, J=13.9 Hz, COCH$_2$Ph), 3.33 (1H, t, J=11.7 Hz), 3.00–2.85 (1H, m), 2.74 (1H, br.d, J=10.3 Hz), 2.65 (1H, dd, J=5.1, 12.5 Hz), 2.60–2.45 (1H, m), 2.45–2.25 (1H, m), 2.25–2.05 (1H, m), 1.70–1.50 (1H, m).
HCL salt: amorphous solid
IR(KBr: 3400, 3100, 1650 cm$^{-1}$.
MS m/z: 443(M+H)$^+$.
Anal. Calcd for C$_{20}$H$_{21}$Cl$_3$N$_2$O$_3$.HCl.0.7H$_2$O: C, 48.74; H, 4.79; N, 5.68.
Found: C, 49.15; H, 5.21; N, 5.58.

EXAMPLE 48

2-(3,4-Dichlorophenyl)-N-hydroxy-N-[2-(3-(S)-hydroxypyrrolidin-1-yl)-1-(S)-(4-methoxyphenyl)ethyl]acetamide and 2-(3,4-dichlorophenyl)-N-hydroxy-N-[2-(3-(S)-hydroxypyrrolidin-1-yl)-1-(R)-(4-methoxyphenyl)-ethyl]acetamide This was prepared from 4-methoxystyrene and 3-(S)-methoxymethyloxypyrrolidine in 5.2% overall yield according to a procedure similar to that described in Examples 7 to 11.

In this case racemization occurred at 1-position to afford the title compounds during the following reactions (mesylation, addition of THPONH$_2$, and acylation).

$^1$H NMR (270 MHz, CDCl$_3$) δ7.40–7.26 (4H, m), 7.12 (0.5H, dd, J=2.2, 8.4 Hz), 7.11 (0.5H, dd, J=2.6, 8.4 Hz), 6.84 (2H, d, J=8.4 Hz), 5.70–5.60 (1H, m, PhCHN), 4.50–4.40 (0.5H, m, CHOH), 4.50–3.00 (2H, almost flat br.s, OH×2), 4.40–4.30 (0.5H, m, CHOH), 3.84 (1H, d, J=14.3 Hz, COCH$_2$Ph), 3.79 (3H, s), 3.73 (1H, d, J=14.7 Hz, COCH$_2$Ph), 3.65–3.40 (1H, m), 3.15–3.00 (1H, m), 2.90–2.40 (4H, m), 2.30–2.10 (1H, m), 1.90–1.78 (0.5H, m), 1.78–1.60 (0.5H, m).
HCl salt: amorphous solid
IR(KBr): 3400, 3150, 1650 cm$^{-1}$.
MS m/z: 438(M$^+$)
Anal. Calcd for C$_{21}$H$_{24}$Cl$_2$N$_2$O$_4$.HCl.2.5H$_2$O: C, 48.43; H, 5.81; N, 5.38.
Found: C, 48.21; H, 5.75; N, 5.35.

EXAMPLE 49

2-(3,4-Dichlorophenyl)-N-hydroxy-N-[2-(3-(S)-hydroxypyrrolidin-1-yl)-1-(S)-(4-trifluoromethylphenyl)ethyl]acetamide This was prepared from 4-trifluoromethylstyrene and 3-(S)-methoxymethyloxypyrrolidine in 25.3% overall yield according to a procedure similar to that described in Examples 7 to 11.

$^1$H NMR (270 MHz, CDCl$_3$) δ7.60–7.35 (6H, m), 7.20–7.10 (1H, m), 5.65 (1H, dd, J=5.5, 11.0 Hz, PhCHN), 4.40–4.30 (1H, m, CHOH), 3.90 (1H, d, J=13.9 Hz, COCH$_2$Ph), 3.73 (1H, d, J=12.5 Hz, COCH$_2$Ph), 3.34 (1H, dd, J=11.0, 12.5 Hz), 3.00–2.90 (1H, m), 2.75–2.65 (2H, m), 2.54 (1H, dd, J=5.1, 10.6 Hz), 2.50–2.00 (4H, m), 1.70–1.55 (1H, m).
IR(neat): 3400, 3250, 1635 cm$^{-1}$.
MS m/z: 476(M$^+$).
HCl salt: amorphous solid.
Anal. Calcd for C$_{21}$H$_{21}$Cl$_2$F$_3$N$_2$O$_3$.HCl.2H$_2$O: C, 45.88; H, 4.77; N, 5.10.
Found: C, 45.90; H, 4.83; N, 4.71.

Preparation 14

(S)-1-(4-Methylphenyl)-1,2-ethanediol 2-tosylate

This prepared from 4-methylstyrene in 75% overall yield according to a procedure similar to that described in Examples 7 and 8. Optical purity was 98.3% ee by HPLC analysis.

$^1$H NMR (270 MHz, CDCl$_3$) δ7.77 (2H, d, J=8.1 Hz), 7.33 (2H, d, J=8.4 Hz), 7.20 (2H, d, J=8.1 Hz), 7.14 (2H, d, J=8.1 Hz), 5.00–4.90 (1H, m), 4.13 (1H, dd, J=3.3, 10.3 Hz), 4.03 (1H, d, J=8.4, 10.3 Hz), 2.49 (1H, d, J=2.9 Hz), 2.45 (3H, s), 1.57 (3H, s).

Preparation 15

(S)-4-Methylstyrene oxide

A mixture of (S)-1-(4-methylphenyl)-1,2-ethanediol2-tosylate (4.13 g, 13.5 mmol) and 50% NaOH aqueous solution (5 ml) in THF (25 ml) was stirred at rt for 1 h and at 50° C. for 2 h. After cooling down to rt, the reaction mixture was diluted with water and extracted with ethyl acetate. The extract was washed with water and brine, dried ($Na_2SO_4$), and concentrated to give 1.59 g (88%) of desired compound as pale brown oil. This oil was used for next reaction without purification.

$^1$H NMR (270 MHz, CDCl3) δ7.20–7.10 (4H, m), 3.83 (1H, dd, J=2.6, 4.0 Hz), 3.13 (1H, dd, J=4.0, 5.5 Hz), 2.80 (1H, dd, J=2.6, 5.5 Hz), 2.34 (3H, s).

Preparation 16

2-(3-(S)-Methoxymethyloxypyrrolidin-1-yl)-1-(S)-(4-methylphenyl)-ethanol and 2-(3-(S)-methoxymethyloxypyrrolidin-1-yl)-2-(R)-(4-methylphenyl)ethanol A mixture of (S)-4-methylstyrene oxide (1.59 g, 11.9 mmol) and 3-(S)-methoxymethyloxypyrrolidine (1.55 g, 11.9 mmol) in isopropanol (25 ml) was refluxed for 7 h. The solvent was evaporated and the residue was purified by column chromatography (silica gel: 150 g, $CH_2Cl_2$/MeOH: 50/1 to 15/1) to give 2.39 g (76%) of desired products as a pale brown oil. This was 3 to 2 mixture of title compounds.
$^1$H NMR (270 MHz, $CDCl_3$) δ7.26 (1.2H, d, J=8.1 Hz), 7.21–7.10 (2.8H, m), 4.75–4.55 (2.6H, m, including 0.6H, d, J=6.6 Hz at 4.66 ppm, 0.6H, d, J=7.0 Hz at 4.63 ppm, 0.4H, d, J=7.0 Hz at 4.62 ppm, 0.4H, d, J=7.0 Hz at 4.58 ppm), 4.35–4.23 (0.6H, m, $OCHCH_2N$), 4.23–4.15 (0.4H, m, $OCHCH_2N$), 3.87 (0.4H, dd, J=6.2, 10.6 Hz, $CHCH_2OH$), 3.77 (0.4H, dd, J=5.9, 10.6 Hz, $CHCH_2OH$), 3.49 (0.4H, dd, J=5.9, 6.2 Hz, NCHPh), 3.38 (1.8H, s), 3.33 (1.2H, s), 3.05–2.90 (1.2H, m), 2.80–2.40 (5H, m), 2.34 (3H, s), 2.25–2.00 (1H, m), 1.95–1.75 (1H, m).

EXAMPLE 50

2-(3,4-Dichlorophenyl)-N-hydroxy-N-[2-(3-(S)-hydroxypyrrolidin-1-yl)-1-(S)-(4-methylphenyl)ethyl]acetamide This was prepared from 2-(3-(S)-methoxymethyloxypyrrolidin-1-yl)-1-(S)-(4-methylphenyl)ethanol and 2-(3-(S)-methoxymethyloxypyrrolidin-1-yl)-2-(R)-(4-methylphenyl)ethanol in 29.5% overall yield according to a procedure similar to that described in Examples 10 and 11.
$^1$H NMR (270 MHz, $CDCl_3$) δ7.40–7.30 (2H, m), 7.23 (2H, app.d, J=8.1 Hz), 7.11 (3H, app.d, J=7.7 Hz), 5.64 (1H, dd, J=5.1, 11.4 Hz, PhCHN), 500–3.00 (2H, almost flat br.s, OH×2), 4.40–4.30 (1H, m, CHOH), 3.84 (1H, d, J=14.7 Hz, $COCH_2Ph$), 3.73 (1H, d, J=14.3 Hz, $COCH_2Ph$), 3.46 (1H, dd, J=11.4, 12.1 Hz), 3.10–2.95 (1H, m), 2.83 (1H, br.d, J=11.0 Hz), 2.75–2.40 (3H, m), 2.32 (3H, s), 2.25–2.10 (1H, m), 1.75–1.60 (1H, m).
HCl salt: amorphous solid
MS m/z: 422(M$^+$)
IR(KBr): 3420, 3180, 1650 cm$^{-1}$.
Anal. Calcd for $C_{21}H_{24}Cl_2N_2O_3 \cdot HCl \cdot 0.5H_2O$: C, 53.80; H, 5.59; N, 5.98.
Found: C, 53.51; H, 5.67; N, 6.04.

Preparation 17

(S)-1-(3-Methoxymethyloxyphenyl)-1,2-ethanediol

This was prepared from 3-methoxymethyloxystyrene (prepared by methoxymethylation of 3-hydroxystyrene in a standard manner) in quantitative yield according to a procedure similar jto that described in Example 7.
$^1$H NMR (270 MHz, $CDCl_3$) δ7.25 (1H, dd, J=7.7, 8.1 Hz), 7.03 (1H, d, J=1.8 Hz), 6.98–6.92 (2H, m), 5.15 (2H, s, $OCH_2OMe$), 4.74 (1H, dd, J=3.3, 8.1 Hz, ArCHOH), 3.71 (1H, br.d, J=9.9 Hz, $CHCH_2OH$), 3.65–3.55 (2H, m, including 1H, dd, J=8.1, 11.0 Hz at 3.61 ppm, $CHCH_2OH$), 3.44 (3H, s, $OCH_2OMe$), 3.14 (1H, br.s, OH).

Preparation 18

(S)-1-(3-Methoxymethyloxyphenyl)-1,2-ethanediol 2-tosylate

This was prepared from (S)-1-(3-methoxymethyloxyphenyl)-1,2-ethanediol in 64% yield according to a procedure similar to that described in Example 8. Its optical purity was 96% ee by HPLC.
$^1$H NMR (270 MHz, $CDCl_3$) δ7.77 (2H, d, J=8.4 Hz), 7.34 (2H, d, J=8.1 Hz), 7.25 (1H, dd, J=7.7, 8.4 Hz), 7.00–6.92 (3H, m), 5.15 (2H, s), 4.95 (1H, ddd, J=3.3, 3.3, 8.4 Hz, ArCHOH), 4.15 (1H, dd, J=3.3, 10.3 Hz, $CHCH_2OTs$), 4.03 (1H, dd, J=8.4, 10.3 Hz, $CHCH_2OTs$), 3.46 (3H, s, $OCH_2OMe$), 2.65 (1H, d, J=3.3 Hz, ArCHOH), 2.45 (3H, s, PhMe).

EXAMPLE 51

2-(3,4-Dichlorophenyl)-N-[1-(S)-(3-methoxymethyloxyphenyl)-2-(3-(S)-tetrahydropyranyloxypyrrolidin-1-yl)ethyl]-N-tetrahydropyranyloxy-acetamide This was prepared from (S)-1-(3-methoxymethyloxyphenyl)-1,2-ethanediol 2-tosylate in 52% overall yield according to the procedure similar to that described in Examples 9 and 10.
$^1$H NMR (270 MHz, $CDCl_3$) δ7.42–6.91 (7H, m), 5.65 (0.5H, dd, J=3.3, 9.9 Hz, PhCHN), 5.54 (0.5H, dd, J=4.4, 11.0 Hz, PhCHN), 5.35–5.25 (1H, m, NOCHO), 5.19 (0.5H, d, J=6.6 Hz, $OCH_2O$), 5.15 (0.5H, d, J=6.6 Hz, $OCH_2O$), 5.14 (0.5H, d, J=7.0 Hz, $OCH_2O$), 5.10 (0.5H, d, J=7.0 Hz, $OCH_2O$), 4.65–4.55 (1H, m, CHOCHO), 4.40–4.30 (0.5H, m, $OCHCH_2N$), 4.30–4.20 (0.5H, m, $OCHCH_2N$), 4.10–3.85 (4H, m, including 0.5H, d, J=16.5 Hz at 4.06 ppm, 0.5H, d, J=16.5 Hz at 3.92 ppm, and 1H, s at 3.92 ppm, $COCH_2Ph$), 3.68–3.15 (6H, m, including each 1.5H, s, at 3.47 and 3.46 ppm, OMe), 3.02–2.80 (2H, m), 2.66–2.35 (3H, m), 2.20–1.15 (14H, m).

EXAMPLE 52

2-(3,4-Dichlorophenyl)-N-hydroxy-N-[1-(S)-(3-hydroxyphenyl)-2-(3-(S)-hydroxypyrrolidin-1-yl) ethyl]acetamide This was prepared from 2-(3,4-dichlorphenyl)-N-[1-(S)-(3-methoxymethyloxyphenyl)-2-(3-(S)-tetrahydropyranyloxypyrrolidin-1-yl)ethyl]-N-tetrahydropyranyloxyacetamide in 46% yield according to the procedure similar to that described in Example 11.
$^1$H NMR (270 MHz, $CDCl_3$ and DMSOd$_6$) δ7.56 (1H, s, PhOH), 7.40 (1H, d, J=1.8 Hz), 7.37 (1H, d, J=8.4 Hz), 7.17 (1H, dd, J=1.8, 8.1 Hz), 7.11 (1H, dd, J=7.7, 8.1 Hz), 6.90–6.70 (3H, m), 5.56 (1H, dd, J=5.1, 10.6 Hz, PhCHN), 4.30–4.20 (1H, m, CHOH), 3.90 (1H, d, J=15.0 Hz, $COCH_2Ph$), 3.74 (1H, d, J=14.5 Hz, $COCH_2Ph$), 4.50–2.50 (2H, almost flat br.s, OH×2), 3.32 (1H, dd, J=11.4, 11.7 Hz), 3.00–2.85 (1H, m), 2.75–2.55 (3H, m, including 1H, dd, J=5.1, 11.0 Hz), 2.40–2.30 (1H, m), 2.15–2.00 (1H, m), 1.80–1.60 (1H, m).

IR(IBr): 3350, 3200, 1630 cm$^{-1}$.

MS m/z: 424(M$^+$)

Free amine: mp 151.6–153.1° C.

Anal. Calcd for $C_{20}H_{22}Cl_2N_2O_4 \cdot 7H_2O$: C, 54.85; H, 5.39; N, 6.40.

Found: C, 54.70; H, 4.99; N, 6.42.

The chemical structures of the compounds prepared in the Examples 1 to 52 are summarized in the following tables.

TABLE

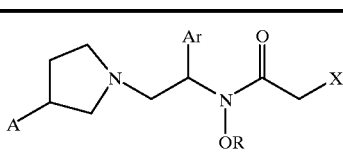

(I)

| Ex. # | A | Ar | R | X |
|---|---|---|---|---|
| 1 | hydrogen | (S)-phenyl | benzyl | 3,4-dichlorophenyl |
| 2 | hydrogen | (S)-phenyl | hydrogen | 3,4-dichlorophenyl |
| 3 | hydrogen | (S)-phenyl | methyl | 3,4-dichlorophenyl |
| 4 | hydrogen | (S)-phenyl | hydrogen | 2,3,6-trichlorophenyl |
| 5 | hydrogen | (S)-phenyl | hydrogen | 4-trifluoromethylphenyl |
| 6 | hydrogen | (S)-phenyl | hydrogen | 1-naphthyl |
| 7 | hydrogen | (S)-phenyl | hydrogen | 2,4,6-trimethylphenyl |
| 8 | hydrogen | (S)-phenyl | hydrogen | 4-pyridyl |
| 9 | hydrogen | (S)-phenyl | hydrogen | benzo[b]furan-4-yl |
| 10 | (S)-tetrahydropyranyloxy | (S)-phenyl | tetrahydropyranyloxy | 3,4-dichlorophenyl |
| 11 | (S)-hydroxy | (S)-phenyl | hydrogen | 3,4-dichlorophenyl |
| 12 | (S)-hydroxy | (S)-4-fluorophenyl | hydrogen | 3,4-dichlorophenyl |
| 13 | (S)-hydroxy | (S)-phenyl | hydrogen | 4-bromophenyl |
| 14 | (S)-hydroxy | (S)-phenyl | hydrogen | 3-bromophenyl |
| 15 | (S)-hydroxy | (S)-phenyl | hydrogen | 4-fluorophenyl |
| 16 | (S)-hydroxy | (S)-phenyl | hydrogen | 3,4-dimethoxyphenyl |
| 17 | (S)-hydroxy | (S)-phenyl | hydrogen | 3-trifluoromethylphenyl |
| 18 | (S)-hydroxy | (S)-phenyl | hydrogen | 4-trifluoromethylphenyl |
| 19 | (S)-hydroxy | (S)-phenyl | hydrogen | 4-biphenyl |
| 20 | (S)-hydroxy | (S)-phenyl | hydrogen | 4-nitrolphenyl |
| 21 | (S)-hydroxy | (S)-phenyl | hydrogen | 3-nitrolphenyl |
| 22 | (S)-hydroxy | (S)-phenyl | hydrogen | 4-chlorophenyl |
| 23 | (S)-hydroxy | (S)-phenyl | hydrogen | 3-chlorophenyl |
| 24 | (S)-hydroxy | (S)-phenyl | hydrogen | 2-chlorophenyl |
| 25 | (S)-hydroxy | (S)-phenyl | hydrogen | 2,3,5-trichlorophenyl |
| 26 | (S)-hydroxy | (S)-phenyl | hydrogen | 2,4,6-trichlorophenyl |
| 27 | (S)-hydroxy | (S)-phenyl | hydrogen | 2,4,6-trimethylphenyl |
| 28 | (S)-hydroxy | (S)-phenyl | hydrogen | 2,3-dichlorophenyl |
| 29 | (S)-hydroxy | (S)-phenyl | hydrogen | 2,4-dichlorophenyl |
| 30 | (S)-hydroxy | (S)-phenyl | hydrogen | 2,5-dichlorophenyl |
| 31 | (S)-hydroxy | (S)-phenyl | hydrogen | 2,6-dichlorophenyl |
| 32 | (S)-hydroxy | (S)-phenyl | hydrogen | 3,5-dichlorophenyl |

TABLE-continued (I)

| Ex. # | A | Ar | R | X |
|---|---|---|---|---|
| 33 | (S)-hydroxy | (S)-phenyl | hydrogen | 2,3,6-trichlorophenyl |
| 34 | (S)-hydroxy | (S)-phenyl | hydrogen | benzo[b]furan-4-yl |
| 35 | (S)-hydroxy | (S)-phenyl | hydrogen | 1-tetralon-6-yl |
| 36 | (S)-hydroxy | (S)-phenyl | hydrogen | 3,4-dimethylphenyl |
| 37 | (S)-hydroxy | (R)-phenyl | hydrogen | 3,4-dichlorophenyl |
| 38 | (S)-hydroxy | (S)-phenyl | hydrogen | 3,4-difluorophenyl |
| 39 | (S)-hydroxy | (S)-phenyl | hydrogen | benzo[b]thiophen-4-yl |
| 40 | (S)-hydroxy | (S)-phenyl | hydrogen | 3,4-methylenedioxyphenyl |
| 41 | (S)-hydroxy | (S)-phenyl | hydrogen | 3,5-difluorophenyl |
| 42 | (R)-tetrahydropyranyloxy | (S)-phenyl | tetrahydropyranyl | 3,4-dichlorophenyl |
| 43 | (R)-hydroxy | (S)-phenyl | hydrogen | 3,4-dichlorophenyl |
| 44 | (R)-hydroxy | (R)-phenyl | hydrogen | 3,4-dichlorophenyl |
| 45 | (S)-methoxymethyloxy | (S)-3-methylphenyl | tetrahydropyranyl | 3,4-dichlorophenyl |
| 46 | (S)-hydroxy | (S)-3-methylphenyl | hydrogen | 3,4-dichlorophenyl |
| 47 | (S)-hydroxy | (S)-4-chlorophenyl | hydrogen | 3,4-dichlorophenyl |
| 48 | (S)-hydroxy | (S)-4-methoxyphenyl | hydrogen | 3,4-dichlorophenyl |
| 49 | (S)-hydroxy | (S)-4-trifluoromethylphenyl | hydrogen | 3,4-dichlorophenyl |
| 50 | (S)-hydroxyl | (S)-4-methylphenyl | hydrogen | 3,4-dichlorophenyl |
| 51 | (S)-tetrahydropyranyloxy | (S)-3-methoxymethyloxyphenyl | tetrahydropyranyl | 3,4-dichlorophenyl |
| 52 | (S)-hydroxy | (S)-3-hydroxyphenyl | hydrogen | 3,4-dichlorophenyl |

What is claimed is:

1. A compound of the following formula

I and a salt thereof wherein

A is hydrogen, hydroxy or OY wherein Y is a hydroxy protecting group selected from benzyl, triphenylmethyl, tetrahydropyrandyl, methoxymethyl and Si, R$^1$, r$^2$, R$^3$ wherein R$^1$, R$^2$ and R$^3$ are each C$_1$–C$_6$ alkyl or phenyl;

Ar is phenyl optionally substituted with one or more substituent selected from halo, hydroxy, C$_1$–C$_4$ alkyl, C$_1$–C$_4$ alkoxy, CF$_3$, C$_1$–C$_4$ alkoxy-C$_1$–C$_4$ alkyloxy and carboxy-C$_1$–C$_4$ alkyloxy;

X is benzofuranyl, benzothiophenyl, and pyridyl, these groups optionally being substituted with up to three substituents selected from halo, $C_1$–$C_4$ alkyl, $C_1$–$C_4$ alkoxy, hydroxy, $NO_2$, $CF_3$ and $SO_2CH_3$; and R is hydrogen, $C_1$–$C_4$ alkyl or a hydroxy protecting group selected from benzyl, triphenylmethyl, tetrahydropyranyl, methoxymethyl and Si, R', $R^2$, $R^3$ wherein R', $R^2$, $R^3$ are each $C_1$–$C_6$ alkyl or phenyl.

2. A compound according to claim 1, wherein A is hydrogen or hydroxy, and R is hydrogen or $C_1$–$C_4$ alkyl.

3. A compound according to claim 2, wherein Ar is phenyl.

4. A compound according to claim 1, wherein A is OY, and R is a hydroxy protecting group, and wherein the hydroxy protecting groups are selected from benzyl, triphenylmethyl, tetrahydropyranyl, methoxymethyl and $R^1R^2R^3Si$, wherein $R^1$, $R^2$ and $R^3$ are each $C_1$–$C_6$ alkyl or phenyl.

5. A pharmaceutical composition useful as an analgesic, or an agent for treatment of stroke or abdominal pain which comprises a compound according to claim 1, and a pharmaceutically inert carrier.

6. A method for the treatment of a medical condition for which agonist activity toward opioid Kappa receptor is needed in a mammalian subject, the method comprises administering to said subject a therapeutically effective amount of a compound according to claim 1.

* * * * *